US009011937B2

(12) United States Patent
Addington et al.

(10) Patent No.: US 9,011,937 B2
(45) Date of Patent: Apr. 21, 2015

(54) **METHOD OF TREATING NEUROLOGICAL CONDITIONS WITH EXTRACT OF *NERIUM* SPECIES OR *THEVETIA* SPECIES**

(75) Inventors: Otis C. Addington, San Antonio, TX (US); Robert A. Newman, Surry, ME (US)

(73) Assignee: Phoenix Biotechnology, Inc., San Antonio, TX (US)

( * ) Notice: Subject to any disclaimer, the term of this patent is extended or adjusted under 35 U.S.C. 154(b) by 0 days.

(21) Appl. No.: 13/288,559

(22) Filed: Nov. 3, 2011

(65) Prior Publication Data

US 2012/0128798 A1 May 24, 2012

Related U.S. Application Data

(63) Continuation-in-part of application No. 12/987,693, filed on Jan. 10, 2011, now Pat. No. 8,481,086, and a continuation-in-part of application No. PCT/US2011/020672, filed on Jan. 10, 2011.

(60) Provisional application No. 61/415,945, filed on Nov. 22, 2010.

(51) Int. Cl.

| | |
|---|---|
| ***A61K 36/00*** | (2006.01) |
| ***A61K 31/704*** | (2006.01) |
| ***A61K 31/7048*** | (2006.01) |
| ***A61K 45/06*** | (2006.01) |

(52) U.S. Cl.
CPC ........... *A61K 31/704* (2013.01); *A61K 31/7048* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,977,174 | A * | 11/1999 | Bradley et al. | 514/549 |
| 6,217,874 | B1 * | 4/2001 | Johannsen | 424/727 |
| 2006/0135443 | A1 | 6/2006 | Khodadoust | |
| 2006/0234955 | A1 | 10/2006 | Pollard | |
| 2007/0154573 | A1 * | 7/2007 | Rashan et al. | 424/725 |
| 2007/0249711 | A1 * | 10/2007 | Choi et al. | 514/557 |
| 2008/0200401 | A1 | 8/2008 | Addington | |

FOREIGN PATENT DOCUMENTS

| | | | |
|---|---|---|---|
| CN | 1301774 | A * | 7/2001 |
| EP | 2260851 | A1 * | 12/2010 |
| WO | WO 9932097 | A2 * | 7/1999 |
| WO | WO 0064921 | A2 * | 11/2000 |
| WO | WO 03099011 | A1 * | 12/2003 |
| WO | 2009/064657 | A1 | 5/2009 |

OTHER PUBLICATIONS

Stroke from Wikipedia, accessed on Aug. 31, 2012, pp. 1-29.*
Rodan et al, Stroke recurrence in children with congenital heart disease. Annals of neurology, (Jul. 2012) vol. 72, No. 1, pp. 103-111.*
Riikonen et al, Hereditary and acquired risk factors for childhood stroke. Neuropediatrics, (Oct. 1994) vol. 25, No. 5, pp. 227-233.*
Dominiczak et al, Genetics of common polygenic stroke. Nature Genetics, (Oct. 1, 2003) vol. 35, No. 2, pp. 116-117.*
Grubb et al, Risks of stroke and current indications for cerebral revascularization in patients with carotid occlusion. Neurosurgery clinics of North America, (Jul. 2001) vol. 12, No. 3, pp. 473-87.*
Jensen et al, The promise and potential pitfalls of serum biomarkers for ischemic stroke and transient ischemic attack. The neurologist, (Jul. 2008) vol. 14, No. 4, pp. 243-246.*
Lasek-Bal et al, Cardiogenic stroke in the young. Postepy w Kardiologii Interwencyjnej, (2012) vol. 8, No. 2, pp. 131-137.*
Rizos et al, Evolution of stroke diagnosis in the emergency room—a prospective observational study. Cerebrovascular diseases (Basel, Switzerland), (2009) vol. 28, No. 5, pp. 448-453.*
Siddiqui et al, Oleanderol, a new pentacyclic triterpene from the leaves of Nerium oleander. Journal of Natural Products (1988) vol. 51, No. 2, pp. 229-233.*
Jaeger et al, Pentacyclic triterpene distribution in various plants- rich sources for a new group of multi-potent plant Extracts. Molecules (2009), 14(6), 2016-2031.*
Karawya et al, Phytochemical study of Nerium oleander growing in Egypt. I. Preliminary investigation. United Arab Republic Journal of Pharmaceutical Sciences (1970), 11(2), 193-209.*
Wang et al. ("Cardiac glycosides provide neuroprotection against ischemic stroke: discovery by a brain slice-based compound screening platform"). Proc. Natl. Acad. Sci. (Jul. 5, 2006), 103:27, pp. 10461-10466.
Yu et al. ("New Polysaccharide from *Nerium indicum* protects neurons via stress kinase signaling pathway") Brain Research, (2007), 1153, pp. 221-230.
Bai et al. ("Studies on Chemical Constituents of Japanese *Nerium indicum* Mill and Their Cytotoxicity in vitro" in J. Anhui Agri. Sci. (2009), 37(20), 9480-9488).
Wang et al. ("LC/MS/MS Analyses of an Oleander Extract for Cancer Treatment" in Anal. Chem. (2000), 72, 3547-3552).

* cited by examiner

*Primary Examiner* — Qiuwen Mi
(74) *Attorney, Agent, or Firm* — Rick Matos; Innovar, L.L.C.

(57) ABSTRACT

A method of treating neurological condition in a subject by administration of an extract, or fraction or sub-fraction thereof, of *Nerium* species or *Thevetia* species is provided, wherein the extract, or fraction or sub-fraction thereof, excludes oleandrin and neriifolin. Alzheimer's disease, Huntington's disease or stroke are treated by administering a therapeutically effective amount of the extract, or a fraction or sub-fraction thereof, to a subject. The extract can be present in a pharmaceutical composition.

30 Claims, 20 Drawing Sheets

METHOD OF TREATING NEUROLOGICAL CONDITIONS WITH EXTRACT OF *NERIUM* SPECIES OR *THEVETIA* SPECIES

CROSS-REFERENCE TO EARLIER FILED APPLICATIONS

The present invention application claims the benefit of U.S. Provisional Application No. 61/415,945 filed Nov. 22, 2010, and claims the benefit of and is a continuation-in-part of U.S. application Ser. No. 12/987,693 filed Jan. 10, 2011 and claims the benefit of and is a continuation-in-part of PCT International Application No. PCT/US11/20672 filed Jan. 10, 2011, the entire disclosures of which are hereby incorporated by reference.

FIELD OF THE INVENTION

The present invention concerns a method of treating neurological conditions with an extract of *Nerium* species or *Thevetia* species, or preparations (compositions, formulations) containing them. In particular, the invention concerns a method for treating neurological disease or disorder by administration of the extract to a subject in need thereof. The invention also includes pharmaceutical compositions containing fractions or sub-fractions of the extract as well as their methods of use and preparation.

BACKGROUND OF THE INVENTION

Neurological diseases and disorders affect brain function. Many efforts have been made to develop curative or ameliorative therapies for these diseases and disorders; however, no comprehensive or universally curative therapy has been developed, even though there are numerous pharmacotherapeutic approaches that have been proven to be effective against various different diseases and disorders.

Huntington's disease (HD) is an inherited disease of the brain that affects the nervous system. It is caused by a defective gene that is passed from parent to child. The HD gene interferes with the manufacture of a particular protein known as 'huntington' which appears to be crucial for proper brain development. The classic signs of HD include emotional, cognitive and motor disturbances. Huntington's is characterized by jerky involuntary movements (chorea), but sometimes causes rigidity without abnormal movements, changes in using the limbs (apraxia), loss of control of bodily functions and dementia, including a progressive deterioration of memory, speed of thought, judgment, and lack of awareness of problems and planning. There is no known cure for Huntington's disease. Although there are a number of medications to help control symptoms associated with HD such as emotional and movement problems, there is no treatment to stop or reverse the course of the disease. Huntington's disease has been recognized as a disease with a general membrane abnormality. A significantly elevated level and activity (10 fold increase) of Na,K-ATPase has been observed in membranes of erythrocytes and basal ganglia of Huntington's patients compared to that of normal (Butterfield D A, Oeswein J Q, Prunty M E, Hisle K C, Markesbery W R). Increased sodium, potassium adenosine triphosphatase activity in erythrocyte membranes in Huntington's disease. Ann Neurology, 4:60-62, 1978) fibroblast membranes obtained from the skin of Huntington's disease patients (Schroeder F, Goetz I E, Roberts E, Membrane anomalies in Huntington's disease fibroblasts. J. Neurochem. 43: 526-539, 1984).

Alzheimer's disease is a form of dementia—a neurodegenerative disease that damages the brain's intellectual functions (memory, orientation, calculation, etc.), but usually preserves its motor functions. In Alzheimer's disease, the mind gradually deteriorates, causing memory loss, confusion, disorientation, impaired judgment and other problems that may affect a person's ability to perform normal daily activities. The type, severity, sequence and progression of mental changes vary greatly. There is no known cure for Alzheimer's disease and no known way to slow its progression. For some people in the early or middle stages of the disease, medication such as tacrine may alleviate some cognitive symptoms. Aricept (donepezil) and Exelon (rivastigmine) are reversible acetylcholinesterase inhibitors that are indicated for the treatment of mild to moderate dementia of the Alzheimer's type. These drugs (called cholinesterase inhibitors) work by increasing the brain's levels of the neurotransmitter acetylcholine, helping to restore communication between brain cells. Some medications may help control behavioral symptoms such as sleeplessness, agitation, wandering, anxiety, and depression. These treatments are aimed at making the patient more comfortable. Although no medication is known to cure Alzheimer's disease, cholinesterase inhibitors may improve performance of daily activities, or lessen behavioral problems. Medications for the treatment of Alzheimer's disease currently being tested include oestrogens, nonsteroidal anti-inflammatory agents, vitamin E, selegiline (Carbex, Eldepryl) and the botanical product gingko biloba.

*Nerium oleander* is an ornamental plant widely distributed in subtropical Asia, the southwestern United States, and the Mediterranean. Its medical and toxicological properties have long been recognized. It has been used, for example, in the treatment of hemorrhoids, ulcers, leprosy, snake bites, and even in the induction of abortion. Oleandrin, an important component but not the sole component of oleander extract, is a cardiac glycoside.

Extraction of glycosides from plants of *Nerium* species has provided pharmacologically/therapeutically active ingredients from *Nerium oleander*. Among these are oleandrin, neriifolin (nerifolin), and other cardiac glycoside compounds. Oleandrin extracts obtained by hot-water extraction of *Nerium oleander*, sold under the trademark ANVIRZEL™, contain the concentrated form or powdered form of a hot-water extract of *Nerium oleander*. A Phase I trial of a hot water oleander extract (i.e. Anvirzel™) has been completed (Mekhail et al., *Am. Soc. Clin. Oncol*., vol. 20, p. 82b, 2001). It was concluded that oleander extracts, which would provide about 57 ug oleandrin/day, can be safely administered at doses up to 1.2 $ml/m^2/d$. No dose limiting toxicities were found.

SUMMARY OF THE INVENTION

The invention provides a method of treating a neurological condition comprising administering to a subject in need thereof a composition containing an extract of *Nerium* species or *Thevetia* species in an effective amount to treat said neurological condition. The invention provides embodiments wherein a fraction of the extract or a sub-fraction of a fraction of the extract is used in place of the unfractionated extract, and wherein the fraction or sub-fraction of the extract excludes oleandrin and neriifolin.

In one aspect, the invention provides a method of treating, in a subject in need thereof, a neurological disease or disorder with a composition comprising an extract of *Nerium* species or *Thevetia* species, the method comprising:

determining that the subject has a neurological disease or disorder; and indicating administration to the subject a composition comprising an extract of *Nerium* species or *Thevetia* species.

Some embodiments of the invention include those wherein: 1) the subject is prescribed and administered a therapeutically relevant dose of the composition; 2) the subject is administered the composition according to a prescribed dosing regimen; 3) the extract comprises one or more therapeutically effective agents extracted from the *Nerium* species or *Thevetia* species; 4) the composition further comprises one or more other therapeutically effective agents; 5) the extract is obtained by extraction of *Nerium* species or *Thevetia* species with hot water, cold water, supercritical fluid, organic solvent or a combination thereof; 6) the extract excludes cardiac glycoside; 7) the extract excludes a therapeutically effective amount of cardiac glycoside; 8) the extract excludes oleandrin; 9) the composition comprises a fraction of an extract of *Nerium* species or *Thevetia* species; 10) the composition comprises a fraction of an extract of *Nerium* species or *Thevetia* species, wherein the fraction has been prepared by liquid chromatographic fractionation of the extract; 11) the *Nerium* species is *Nerium oleander* and the *Thevetia* species is *Thevetia neriifolia;* 12) the extract excludes a neriifolin; 13) the composition comprises a sub-fraction of a fraction of an extract of *Nerium* species or *Thevetia* species, wherein the sub-fraction has been prepared by liquid chromatographic fractionation of a fraction of the extract, and the sub-fraction excludes oleandrin and neriifolin; 14) the extract of *Nerium* species or *Thevetia* species, if it contains cardiac glycoside, provides an improved clinical response or clinical effect when administered in a dosage form to a subject having neurological disease or disorder as compared to pure cardiac glycoside administered in an otherwise similar dosage form to the subject at the same dose of cardiac glycoside; or 15) a combination thereof.

The invention also provides a method of treating a neurological condition in a subject in need thereof comprising:

determining whether or not the neurological condition in the subject is Alzheimer's disease, Huntington's disease, stroke or other neurological condition;

indicating administration of an extract of *Nerium* species or *Thevetia* species;

administering an initial dose of the extract to the subject according to a prescribed initial dosing regimen for a period of time;

periodically determining the adequacy of the subject's clinical response and/or therapeutic response to treatment with the extract; and if the subject's clinical response and/or therapeutic response is adequate, then continuing treatment with extract as needed until the desired clinical endpoint is achieved; or if the subject's clinical response and/or therapeutic response are inadequate at the initial dose and initial dosing regimen, then escalating or deescalating the dose until the desired clinical response and/or therapeutic response in the subject is achieved.

The invention also provides a method of preventing or reducing the incidence of occurrence of a neurological condition in a population of subjects at risk thereof, the method comprising:

administering an effective dose of extract of *Nerium* species or *Thevetia* species on a recurring basis for an extended period of time to one or more subjects in a population of subjects at risk of suffering from a neurological condition such as Alzheimer's disease, Huntington's disease, stroke or other neurological condition, thereby preventing or reducing the incidence of the neurological condition in the population.

The invention includes embodiments wherein: a) the method further comprises indicating administration of the extract to the one or more subjects; b) the method further comprises administering an effective dose of the extract to the subject according to a prescribed dosing regimen for a period of time; c) the method further comprises periodically determining the adequacy of one or more subject's clinical response and/or therapeutic response to treatment with the extract; d) if the subject's clinical response and/or therapeutic response is adequate, then the method further comprises continuing treatment with the extract as needed until the desired clinical endpoint is achieved; e) if the subject's clinical response and/or therapeutic response are inadequate at the initial dose and initial dosing regimen, then the method further comprises escalating or deescalating the dose until the desired clinical response and/or therapeutic response in the subject is achieved; f) the extract is administered to plural subjects in a population; g) the recurring basis is daily, every other day, every second day, every third day, every fourth day, every fifth day, every sixth day, weekly, every other week, every second week, every third week, monthly, bimonthly, semi-monthly, every other month every second month, quarterly, every other quarter, trimesterly, seasonally, semi-annually and/or annually; h) the extended period is one or more weeks, one or more months, one or more quarters and/or one or more years; i) the effective dose is administered one or more times in a day; j) the method further comprises identifying a population of subjects at risk of suffering from a neurological condition such as Alzheimer's disease, Huntington's disease, stroke or other neurological condition; k) the population of subjects at risk is characterized by advancing age of the subject, familial history of the neurological condition, genetic predisposition to occurrence of neurological condition, the presence and expression of ApoE4 gene in the subject, female gender (twice as many women get Alzheimer's disease than men), cardiovascular disease (e.g. high blood pressure and high cholesterol levels), diabetes (especially Type 2 or adult onset forms of this disease), Down's Syndrome, head injury, low levels of formal education, smoking, excessive alcohol consumption and/or drug abuse; l) the extract excludes a therapeutically effective amount of cardiac glycoside; m) the extract excludes cardiac glycoside; or n) a combination thereof.

The invention also provides a time-delayed method of treating stroke in a subject comprising:

within a delay period after a subject has suffered the stroke, administering an initial dose of extract of *Nerium* species or *Thevetia* species according to an initial dosing regimen;

determining the adequacy of subject's clinical response and/or therapeutic response to treatment with the extract; and if the subject's clinical response and/or therapeutic response is adequate, then continuing treatment with extract as needed until the desired clinical endpoint is achieved; or if the subject's clinical response and/or therapeutic response are inadequate at the initial dose and initial dosing regimen, then escalating or deescalating the dose until the desired clinical response and/or therapeutic response in the subject is achieved.

Some embodiments of the invention include those wherein: 1) the delay period is 10 hours or less, 8 hours or less, 6 hours or less, 4 hours or less, 3 hours or less, 2 hours or less, 1 hour or less, 45 minutes or less, 30 minutes or less, 20 minutes or less or 10 min or less; 2) determining the adequacy of a subject's clinical and/or therapeutic response is done by assessments of any weakness of the face, arm and/or leg on one side of the body, numbness in the face, arm, and/or leg on one side of the body, inability to understand spoken language, inability to speak or speak clearly, inability to write, vertigo and/or gait imbalance, double vision and an unusually severe headache; or 3) a combination thereof.

The invention also provides use of an extract of *Nerium* species or *Thevetia* species in the manufacture of a medicament for the treatment of a neurological condition in a subject. In some embodiments, the manufacture of such a medicament comprises: providing an extract of *Nerium* species or *Thevetia* species; including a dose of extract of *Nerium* species or *Thevetia* species, or a fraction thereof, in a pharmaceutical dosage form; and packaging the pharmaceutical dosage form. The invention also provides a pharmaceutical composition comprising an extract of *Nerium* species or *Thevetia* species for the treatment of a neurological condition in a subject. In some embodiments, the manufacture can be conducted as described in PCT International Application No. PCT/US06/29061 filed Jul. 26, 22006, U.S. Pat. No. 7,402,325 filed Jul. 28, 2005, or U.S. Ser. No. 12/019,435 filed Jan. 24, 2008, the entire disclosures of which are hereby incorporated by reference. The manufacture can also include one or more additional steps such as: delivering the packaged dosage form to a vendor (retailer, wholesaler and/or distributor); selling or otherwise providing the packaged dosage form to a subject having a neurological condition; including with the medicament a label and a package insert, which provides instructions on use, dosing regimen, administration, content and toxicology profile of the dosage form. In some embodiments, the treatment of a neurological condition comprises: determining that a subject has a neurological disease or disorder; indicating administration of the extract, or a fraction thereof, to the subject according to a dosing regimen; administering to the subject one or more pharmaceutical dosage forms containing the extract, wherein the one or more pharmaceutical dosage forms is administered according to the dosing regimen.

The invention also provides an extract of *Nerium* species or *Thevetia* species, or a composition, i.e. a pharmaceutical formulation or dosage form, comprising an extract of *Nerium* species or *Thevetia* species for the treatment of a neurological condition. In some embodiments, the extract can be obtained from *Nerium* species or *Thevetia* species as described herein or in U.S. Pat. No. 7,402,325, PCT International Application No. PCT/US06/29061, U.S. application Ser. No. 12/019,435, or Newman et al. (*Mol. Interven.* (2008), 8, 36-49), the entire disclosures of which are hereby incorporated by reference.

The invention provides a method for preparing a fraction of extract of *Nerium* species or *Thevetia* species comprising: extracting a mass comprising *Nerium* species or *Thevetia* species to form an unfractionated extract thereof, the extract comprising one or more pharmacologically active components for the treatment of a neurological condition; and fractionating the unfractionated extract to form two or more fractions thereof, wherein at least one fraction comprises one or more non-cardiac glycoside pharmacologically active components. In some embodiments, a) at least one fraction excludes cardiac glycoside; b) at least one fraction further comprises cardiac glycoside; c) the extraction is conducted with supercritical fluid, water, organic solvent or a combination thereof; d) the fractionation is conducted by liquid chromatography or solvent extraction; e) the at least one fraction excludes oleandrin and neriifolin; or f) a combination thereof.

The invention also provides a method of fractionating an extract of *Nerium* species or *Thevetia* species in order to provide one or more therapeutically effective fractions thereof. The method comprises: a) providing an extract of *Nerium* species or *Thevetia* species; b) fractionating the extract to provide two or more different fractions of the extract, a first extract fraction comprising one or more pharmacologically active agents, which is/are not a cardiac glycoside, and excluding cardiac glycoside (oleandrin and neriifolin), and a second extract fraction comprising one or more cardiac glycosides and one or more pharmacologically active agents, which is/are not a cardiac glycoside. The fractionation can also be performed as described herein. In some embodiments, the first or second extract fraction is subjected to further fractionation to provide two or more different sub-fractions, wherein a first sub-fraction comprises one or more steroids and a second sub-fraction comprises one or more triterpenes. In some embodiments, the fractionation is performed by liquid chromatography with a stationary phase and a mobile phase.

The invention also provides a composition comprising a fraction of an extract obtained from *Nerium* species or *Thevetia* species, whereby the fraction has been obtained by fractionation of the extract obtained from *Nerium* species or *Thevetia* species. In some embodiments, a fraction of extract comprises one or more steroids and one or more tritepenes and optionally excludes cardiac glycoside (oleandrin and neriifolin).

The invention also provides a composition comprising a sub-fraction of fraction of an extract obtained from *Nerium* species or *Thevetia* species, whereby the sub-fraction has been obtained by further fractionation of a fraction of the extract obtained from *Nerium* species or *Thevetia* species. In some embodiments, a sub-fraction of a fraction of extract comprises one or more steroids, cardiac glycosides, the associated aglycones of cardiac glycosides, e.g. oleandrigenin, cardenolides, or triterpenoids, and one or more tritepenes. In some embodiments, a sub-fraction of a fraction of extract comprises one or more triterpenes and excludes a steroid. Each sub-fraction independently optionally excludes cardiac glycoside (oleandrin and neriifolin).

In some embodiments: a) the extract further comprises at least two pharmacologically active agents obtained (extracted) from *Nerium* species or *Thevetia* species; b) the at least two pharmacologically active agents function additively or synergistically to contribute to the therapeutic efficacy of the extract when the extract is administered to a subject; c) none of the at least two pharmacologically active agents is a cardiac glycoside; and/or d) at least two pharmacologically active agents are selected from the group of cardiac glycosides, the associated aglycones of cardiac glycosides, e.g. oleandrigenin, cardenolides or triterpenoids.

In some embodiments: 1) the cardiac glycoside is selected from the group consisting of oleandrin, odoroside, neritaloside, ouabain, bufalin, digitoxin, cinobufatalin, cinobufagin, and resibufogenin; 2) the extract is present in a pharmaceutical formulation or composition; 3) the extract has been obtained from an oleander plant mass or neriifolia plant mass; 4) the plant mass comprises *Nerium* species, such as *Nerium oleander*, or *Thevetia* species, such as *Thevetia neriifolia* or *Thevetia peruviana* (otherwise known as yellow oleander); 5) the extract was prepared by supercritical fluid (SCF) extraction optionally in the presence of a modifier; 6) the cardiac glycoside is oleandrin; 7) the extract was prepared by hot water extraction, cold water extraction, organic solvent extraction or aqueous organic solvent extraction.

In some embodiments, the extract (or fraction or sub-fraction thereof) comprises less than 1% wt., less than 0.5% wt., less than 0.1% wt., less than 0.05% wt. or less than 0.01% wt. of polysaccharide. In some embodiments, the extract (or fraction or sub-fraction thereof) comprises betulin (urs-12-ene-3β,28-diol); 28-norurs-12-en-3β-ol; urs-12-en-3β-ol; 3β,3β-hydroxy-12-oleanen-28-oic acid; 3β,20α-dihydroxyurs-21-en-38-oic acid; 3β,27-dihydroxy-12-ursen-38-oic acid; 3β,13β-dihydroxyurs-11-en-28-oic acid; 3β,12α-dihydroxy-oleanan-28,13β-olide; and 3β,27-dihydroxy-12-oleanan-28-oic acid. In some embodiments, the extract (or fraction or sub-fraction thereof) comprises one or more cardiac glycoside precursors selected from a glycone constituent of a cardiac glycoside. In some embodiments, the glycone is selected from the group consisting of glucoside, fructoside, and glucuronide. In some embodiments, the extract (or fraction or sub-fraction thereof) comprises oleandrigenin, ursolic acid, betulinic acid, odoroside, neritaloside, oleanolic acid and one or more triterpenes and less than 0.5% by weight polysaccharide.

In some embodiments, the subject having a neurological condition, i.e. the subject in need thereof, is part of a population of such subjects. The invention provides a method for improving the clinical status of a statistically significant number of subjects of in a population of subjects having a neurological condition, the method comprising: administering to the population of subjects an extract of *Nerium* species or *Thevetia* species or a composition comprising an extract of *Nerium* species or *Thevetia* species; and determining the clinical status of the subjects. In some embodiments, the statistically significant number is at least 5% of the population.

In some embodiments, the neurological condition is Alzheimer's disease, Huntington's disease, stroke, a tauopathy or other neurological condition, such as described herein. The medicament can be manufactured by inclusion of the extract in a pharmaceutical dosage form containing one or more pharmaceutically acceptable excipients.

Treatment of the subject with the extract or composition containing the extract is continued as needed. The dose or dosing regimen can be adjusted as needed until the patient reaches the desired clinical endpoint(s) such as a reduction or alleviation of specific neurological symptoms associated with the disease. Determination of the adequacy of clinical response and/or therapeutic response can be conducted by a clinician familiar with the neurological condition being treated.

In some embodiments, the neurological condition is selected from the group consisting of neurological disease, neurological disorder, tauopathy, and stroke. In some embodiments, the neurological disease is a neurodegenerative disease. In some embodiments, the neurodegenerative disease is selected from the group consisting of Huntington's disease, Alzheimer's disease, Parkinson's disease, amyotrophic lateral sclerosis, bovine spongiform encephalopathy, multiple sclerosis, diabetic neuropathy, autism and juvenile neuronal ceroid lipofuscinosis. In some embodiments, stroke is stroke-mediated ischemic injury. In some embodiments, the neurological condition is a tauopathy, which is a neurodegenerative disease having an etiology associated with an imbalance in the Tau3R/Tau4R ratio in a subject. Tauopathies are a class of neurodegenerative diseases resulting from the pathological aggregation of tau proteins in the human brain. In some embodiments, the tauopathy is Down's syndrome, Pick's disease, corticobasal degeneration, some variants of prions disease, Alzheimer's disease, progressive supranuclear palsy or frontotemporal dementia. The individual steps of the methods of the invention can be conducted at separate facilities or within the same facility.

In some embodiments, the neurons are in vitro, ex vivo or in vivo. In some embodiments, the neurons are CA-1 neurons.

In some embodiments, the invention provides an extract, or fraction thereof or sub-fraction thereof, of *Nerium* species or *Neriifolia* species, having a $^1$HNMR spectrum as described herein. In some embodiments, the invention provides an extract, or fraction thereof or sub-fraction thereof, of *Nerium* species or *Neriifolia* species, exhibiting therapeutic activity as described herein when administered to a subject. In some embodiments, the invention provides an extract, or fraction thereof or sub-fraction thereof, of *Nerium* species or *Neriifolia* species, having a HPLC chromatogram as described herein. In some embodiments, the methods of the invention employ an extract, fraction thereof or sub-fraction thereof, as described herein. In some embodiments, the compositions of the invention comprise an extract, fraction thereof or sub-fraction thereof, as described herein.

The invention includes all combinations of the aspects, embodiments and sub-embodiments of the invention disclosed herein. Unless otherwise specified herein, the term "extract" can refer to the unfractionated extract or fractionated extract, i.e. a fraction of the extract, or sub-fractionated extract, i.e. a sub-fraction of a fraction of the extract.

BRIEF DESCRIPTION OF THE FIGURES

The following figures form part of the present description and describe exemplary embodiments of the claimed invention. The skilled artisan will, in light of these figures and the description herein, be able to practice the invention without undue experimentation.

FIG. 9A depicts the HNMR spectrum of the O-4 fraction before sub-fractionation according to Example 17. FIGS. 9B-9I depict the HNMR spectra for various sub-fractions obtained by silica gel flash chromatography, according to Example 17, performed on the O-4 fraction.

DETAILED DESCRIPTION OF THE INVENTION

Figure 1A:
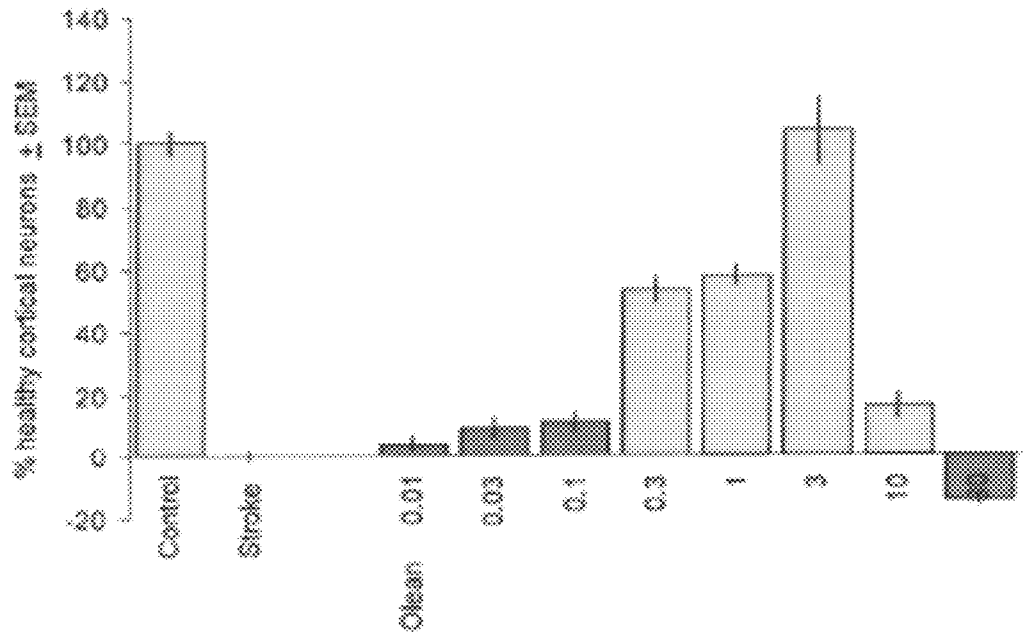
FIG. 1A depicts concentration-response data obtained from the comparative evaluation of the oleandrin versus no oxygen or glucose deprivation (OGD), the control, in a neuroprotection brain-slice-based "stroke" assay (Example 8), wherein the number of healthy cortical neurons is determined following 5-6 minutes of oxygen and glucose deprivation (OGD=stroke) in the presence or absence of oleandrin.

The invention provides a method of treating a neurological condition by administration of an effective dose of extract of *Nerium* species or *Thevetia* species to a subject in need thereof. The extract is administered according to a dosing regimen best suited for the subject, the suitability of the dose and dosing regimen to be determined clinically according to conventional clinical practices and clinical treatment endpoints for the neurological condition being treated.

In some embodiments, the neurodegenerative disorder or neurological condition being treated has an etiology associated with an over-expression of tau proteins and/or an imbalance in the Tau3R/Tau4R ratio in a subject. Such a condition is termed a tauopathy. Exemplary tauopathies include Down's syndrome, Pick's disease, some variants of prions disease, Alzheimer's disease, progressive supranuclear palsy or frontotemporal dementia, corticobasal degeneration, Guam parkinsonism dementia complex, dementia with argyrophilic grains, Niemann-Pick disease Type C, and dementia pugilistic.

In some embodiments, the neurodegenerative disorder or neurological condition being treated has an etiology associated with abnormal or atypical proteolysis of amyloid beta precursor protein, accumulation of amyloid beta protein in the synapses of the neurons, formation of amyloid fibrils in the synapses of the neurons, or formation of amyloid plaques in the synapses of the neurons. Exemplary of such disorders or conditions is Alzheimer's disease. A subject treated according to the invention will exhibit a therapeutic response. By "therapeutic response" is meant that a subject suffering from the disease or disorder will enjoy at least one of the following clinical benefits as a result of treatment with the extract: amelioration of the disease or disorder, reduction in the occurrence of symptoms associated with the disease or disorder, partial remission of the disease or disorder, full remission of the disease or disorder, or increased time to progression. In other words, the therapeutic response can be a full or partial therapeutic response.

A therapeutic response can also be described as one in which the quality of life of the patient afflicted with the neurodegenerative disease is improved. Improvement in quality of life may occur, for example, through a reduction in occurrence, frequency or severity of symptoms associated with the disease (e.g. tremors, involuntary muscle movements, loss or partial loss of nerve-muscle coordination, memory retention, etc.).

"Preventing occurrence of a neurological condition in a population of subjects at risk" means that the neurological condition will not occur during a predetermined time period in a demographically predetermined population of subjects that are at risk of suffering from the neurological condition. The prevention during the predetermined time period occurs as a result of subjects in that population having been administered an extract according to the invention. As one example, when an extract or extract-containing composition is administered for a predetermined time period to subjects in a population of subjects at risk of suffering from stroke, stroke will not occur in those subjects during the predetermined time period. In particular, an extract-containing composition is chronically administered over a period of one year to a population of subjects at risk of suffering from Alzheimer's disease or any of the tauopathology related diseases, and the subjects in that population do not exhibit symptoms associated with Alzheimer's during that one-year period.

"Reducing the incidence of occurrence of a neurological condition in a population of subjects at risk" is related in meaning to "preventing the incidence", except that "reducing the incidence of occurrence" permits the occurrence of the neurological condition in a demographically predetermined population of subjects but at a rate of occurrence or a level of severity that is reduced as compared to an otherwise demographically similar predetermined population of subjects at risk not being administered the extract-containing composition according to the invention.

As used herein, "time to progression" is the period, length or duration of time after a disease is diagnosed (or treated) until the disease begins to worsen. It is the period of time during which the level of a disease is maintained without further progression of the disease, and the period of time ends when the disease begins to progress again. Progression of a disease is determined by "staging" a subject suffering from a neurological condition prior to or at initiation of therapy. For example, the subject's neurological health is determined prior to or at initiation of therapy. The subject is then treated with the extract, and the neurological health monitored periodically. At some later point in time, the symptoms of the neurological condition may worsen, thus marking progression of the disease and the end of the "time to progression". The period of time during which the disease did not progress or during which the level or severity of the disease did not worsen is the "time to progression".

A dosing regimen includes a therapeutically relevant dose (or effective dose) of extract administered according to a dosing schedule. A therapeutically relevant dose, therefore, is a therapeutic dose at which a therapeutic response of the disease or disorder to treatment with extract is observed and at which a subject can be administered the extract without an excessive amount of unwanted or deleterious side effects. A therapeutically relevant dose is non-lethal to a subject, even though it may cause some side effects in the patient. It is a dose at which the level of clinical benefit to a subject being administered the extract exceeds the level of deleterious side effects experienced by the subject due to administration of the extract. A therapeutically relevant dose will vary from subject to subject according to a variety of established pharmacologic, pharmacodynamic and pharmacokinetic principles. However, a therapeutically relevant dose will typically be in the range of 0.1 to 100 micrograms of extract/day, the extract being in either solid, liquid or semisolid form. It is known in the art that the actual amount of a pharmacologically active agent required to provide a target therapeutic result in a subject may vary from subject to subject according to the basic principles of pharmacy.

A therapeutically relevant dose can be administered according to any dosing regimen typically used in the treatment of neurological or neurodegenerative diseases or disorders. A therapeutically relevant dose can be administered once, twice, thrice or more daily dosing schedule. It can be administered every other day, every third day, every fourth day, every fifth day, semiweekly, weekly, biweekly, every three weeks, every four weeks, monthly, bimonthly, semimonthly, every three months, every four months, semiannually, annually, or according to a combination of any of the above to arrive at a suitable dosing schedule. For example, a therapeutically relevant dose can be administered once daily for one or more weeks.

The examples below include evidence of the efficacy of the extract in neurological conditions such as neurological diseases, neurological disorders and stroke. Example 3 details a method of treating Alzheimer's disease with a *Nerium* species extract, or composition thereof, *Thevetia* species extract, or composition thereof, or a combination thereof with one or more other therapeutic agents. Example 4 details a method of treating Huntington's disease with the extract or a combination of the extract with one or more other therapeutic agents. Example 5 details a method of treating stroke-mediated and non-stroke mediated ischemic brain injury with the extract or a combination of the extract with one or more other therapeutic agents.

In general, a subject having a neurological condition is treated as follows. A subject presenting with a neurological condition is evaluated to determine whether or not the neurological condition is Alzheimer's disease, Huntington's disease, stroke or other neurological condition. If the subject has a positive diagnosis, administration of the extract or extract-containing composition is indicated. Initial doses of the extract or composition are administered to the subject according to a prescribed dosing regimen for a period of time. The subject's clinical response and level of therapeutic response are determined periodically. If the level of therapeutic response is too low at one dose, then the dose is escalated according to a predetermine dose escalation schedule until the desired level of therapeutic response in the subject is achieved. If the subject exhibits undesirable side effects or an unacceptable level of side effects, then the dose is deescalated until the desired balance of level of therapeutic response versus side effect profile in the subject is achieved. Treatment of the subject with the extract or composition is continued as needed. The dose or dosing regimen can be adjusted as needed until the patient reaches the desired clinical endpoint(s) such as cessation of the disease itself, reduction in disease associated symptoms, and/or a reduction in the progression of the disease process.

The extract, in particular unfractionated extract, comprises one or more pharmacologically active compounds. Some of those compounds are as yet unidentified and some can be oleandrin or other cardiac glycosides, oleaside, oleandrigenin, neritaloside, odoroside (Wang X, Plomley J B, Newman R A and Cisneros A. LC/MS/MS analyses of an oleander extract for cancer treatment, *Analytical Chem.* 72: 3547-3552, 2000), and other plant materials. Unfractionated SCF extract from a supercritical fluid process typically contains a theoretical range of 0.9% to 2.5% by weight of oleandrin. SCF extracts comprising varying amount of oleandrin have been obtained. In one embodiment, the SCF extract comprises about 2% by wt. of oleandrin.

The extractable unidentified components of the extract of *Nerium* species or *Thevetia* species can comprise at least one (non-cardiac glycoside) pharmacologically active component that contributes to the efficacy of the SCF extract or a fraction thereof. Two or more pharmacologically active extractable components can function additively or synergistically to provide the observed efficacy. In other words, the *Nerium* species or *Thevetia* species extract of the invention comprises one or more pharmacologically active components that are not a cardiac glycoside, even though one or more cardiac glycosides can additionally be included in the extract. The extract can be fractionated into various different fractions some of which contain cardiac glycoside, one or more non-cardiac glycoside pharmacologically active components or a combination thereof. In addition, each fraction of extract can be further fractionated into two or more different sub-fractions.

Figure 1B:
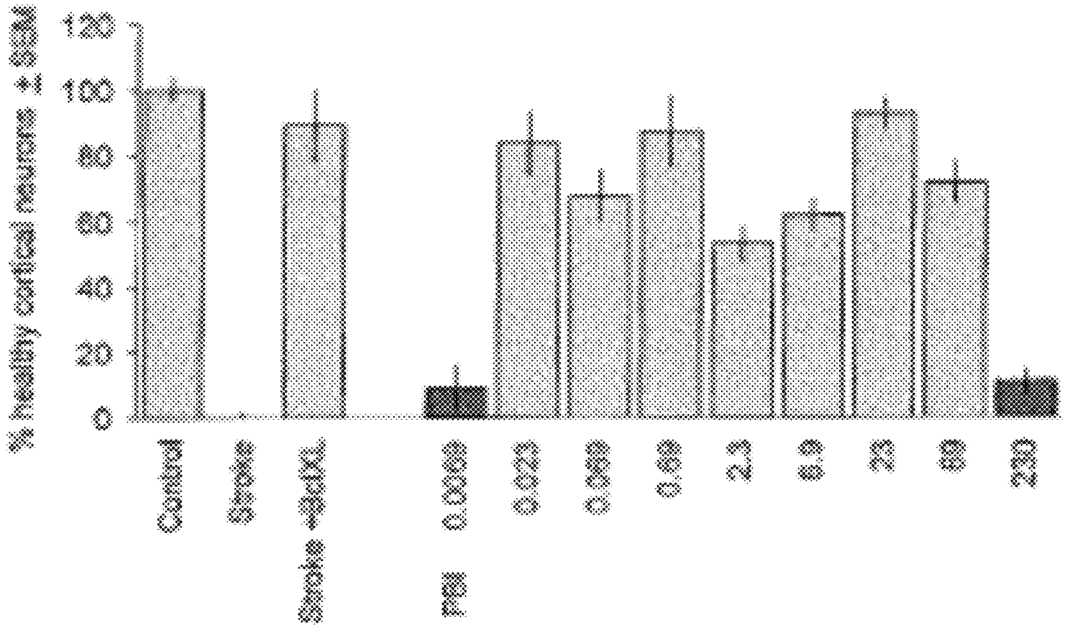
FIG. 1B depicts results of a concentration-response assay for unfractionated SCF extract of *Nerium oleander* in a neuroprotection brain-slice-based "stroke" assay as described herein (Example 8), wherein no oxygen or glucose deprivation is used as the control.

Evidence of the existence of one or more pharmacologically active components, other than oleandrin, in the SCF extract was obtained by comparing the concentration-response curves for a solution containing pure oleandrin versus one containing the SCF extract. FIG. 1A depicts the results of a concentration-response assay for a solution containing pure oleandrin in a neuroprotection brain-slice-based "stroke" assay as described in Example 8. The concentration of oleandrin in the solution was varied from 0.0069 to 230 μg/ml. FIG. 1B depicts results of a concentration-response assay for an oleandrin-containing SCF *Nerium* species extract in a neuroprotection brain-slice-based "stroke" assay as described herein (Example 8). The data demonstrate that the extract is more efficacious that pure oleandrin meaning the extract contains one or more pharmacologically active agents that provide neuroprotection.

Example 8 provides a detailed description of an in vitro assay used to evaluate the efficacy of the extract, or composition thereof, for the treatment of stroke-mediated ischemic neuronal injury. The assay is a brain slice-based assay for oxygen and glucose deprivation (OGD) used to induce 50% loss of healthy cortical neurons by 24 hours. The parent unfractionated SCF extract of *Nerium* species, e.g. *Nerium oleander*, is used as a positive control. The parent extract is then fractionated according to Example 13 to provide a fraction of extract of *Nerium* species. The fractions are analyzed according to Examples 6, 14 and 17.

Figure 9A:
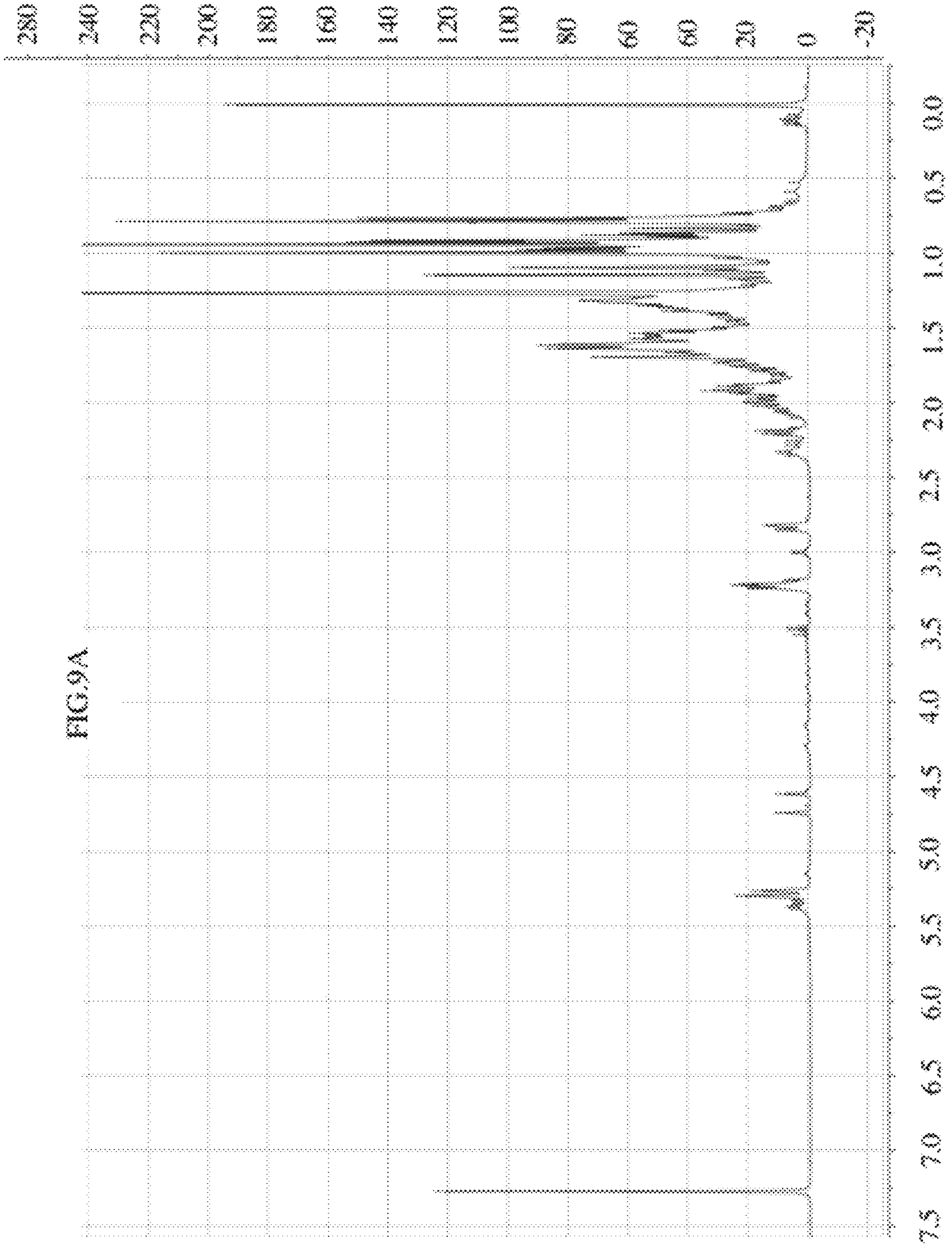
FIGS. 9A-9I depict HNMR spectra for various components present in the fraction O-4 *Nerium oleander* SCF extract.
Figure 9B:
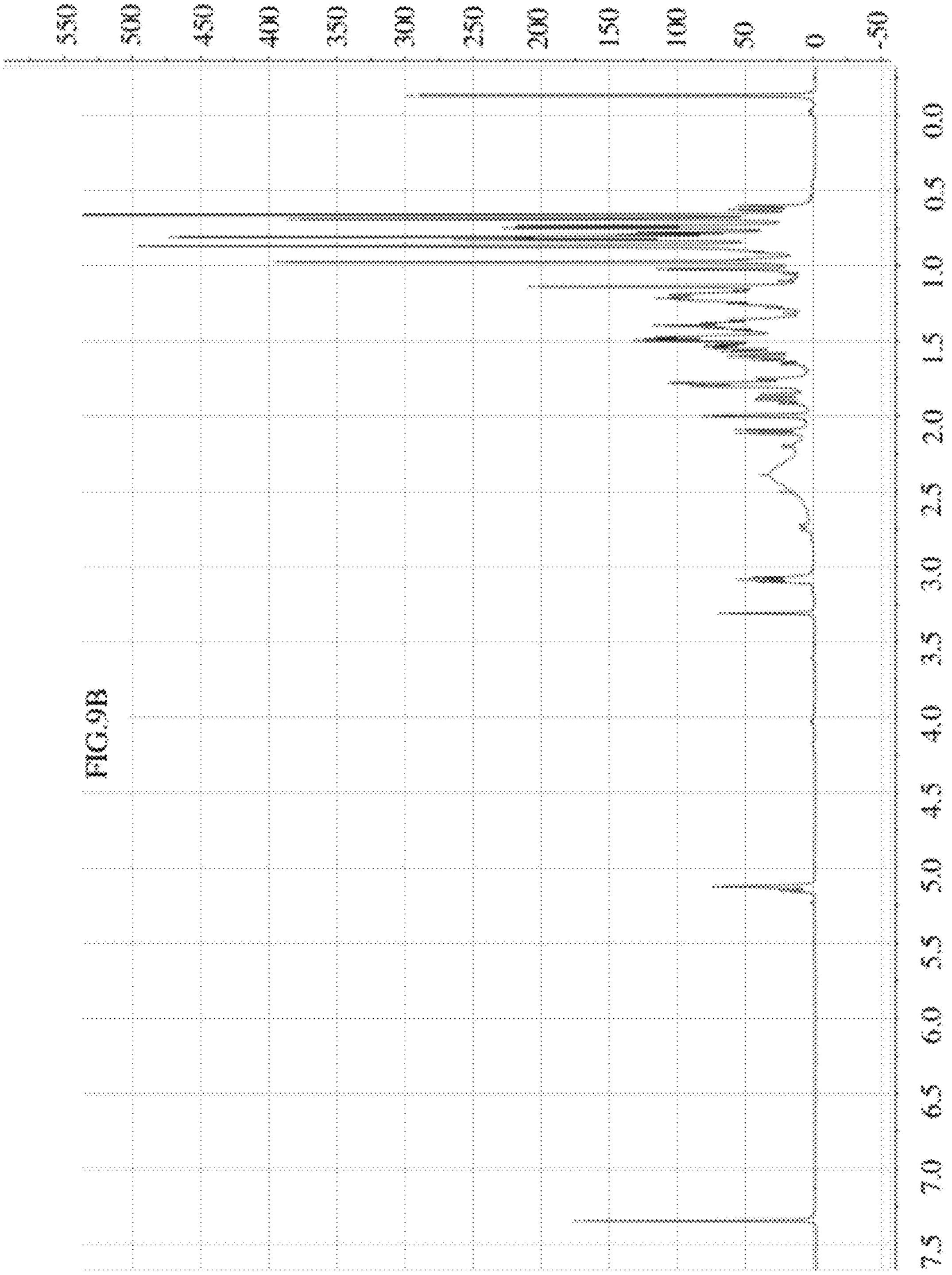
Figure 9C:
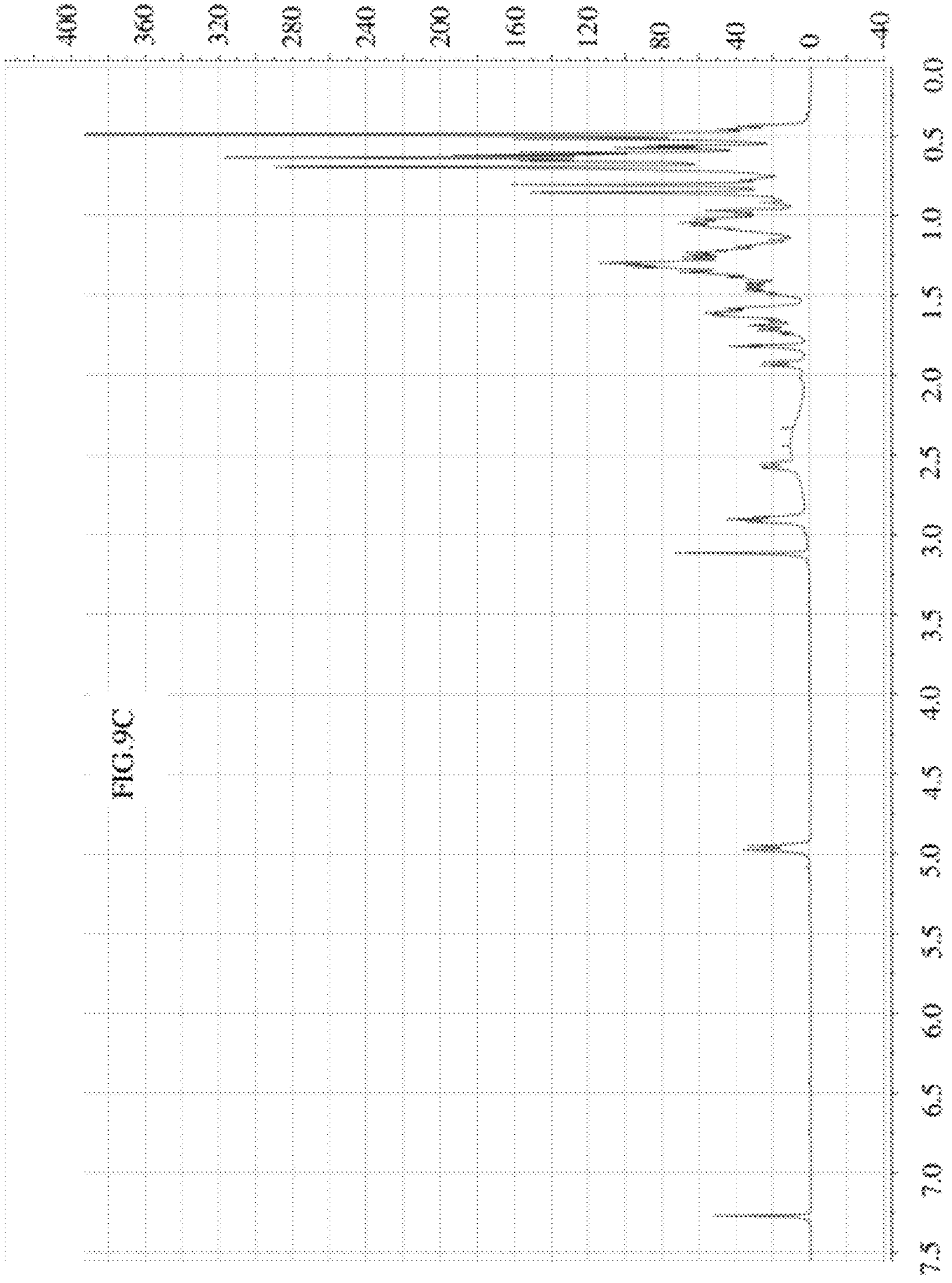
Figure 9D:
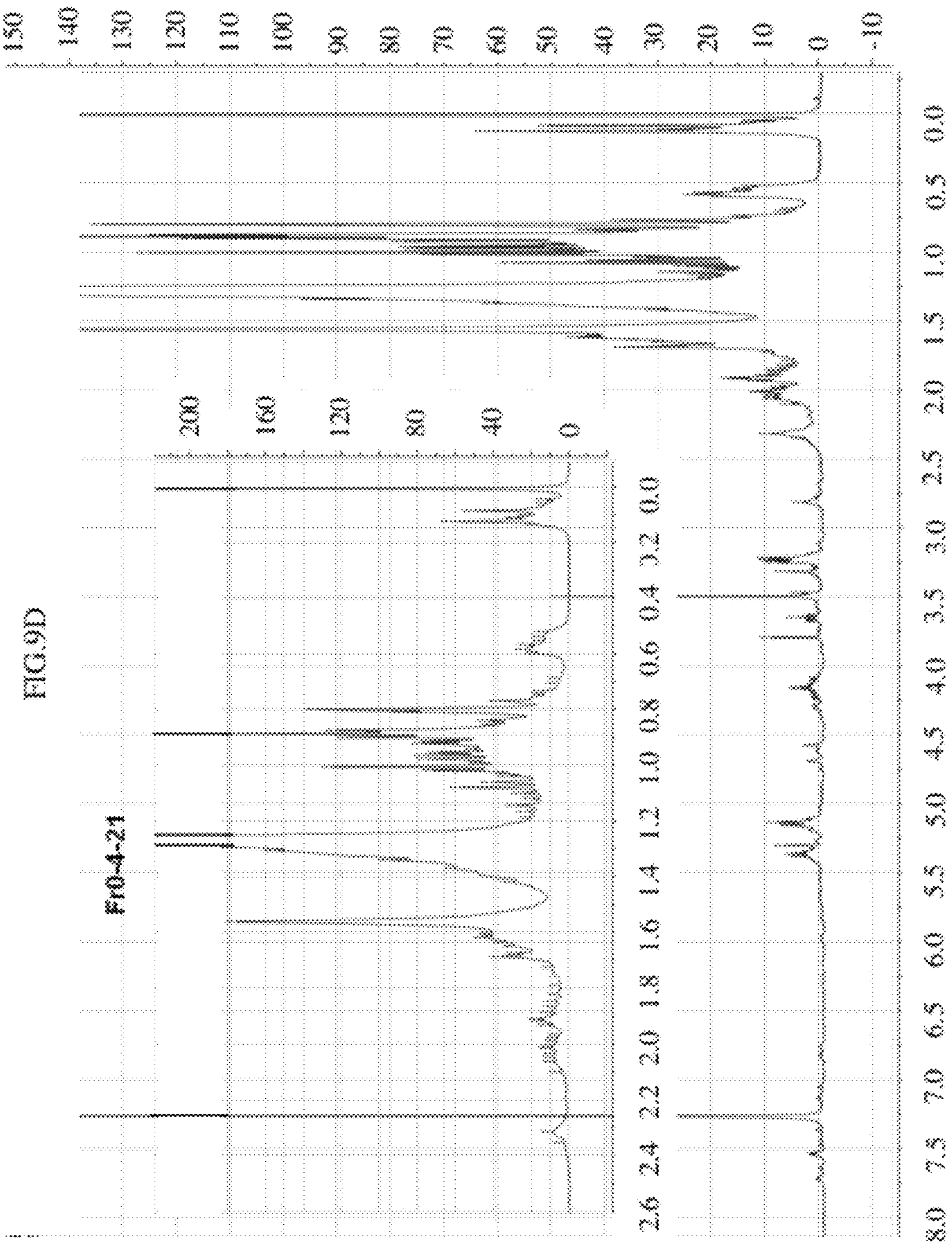
Figure 9E:
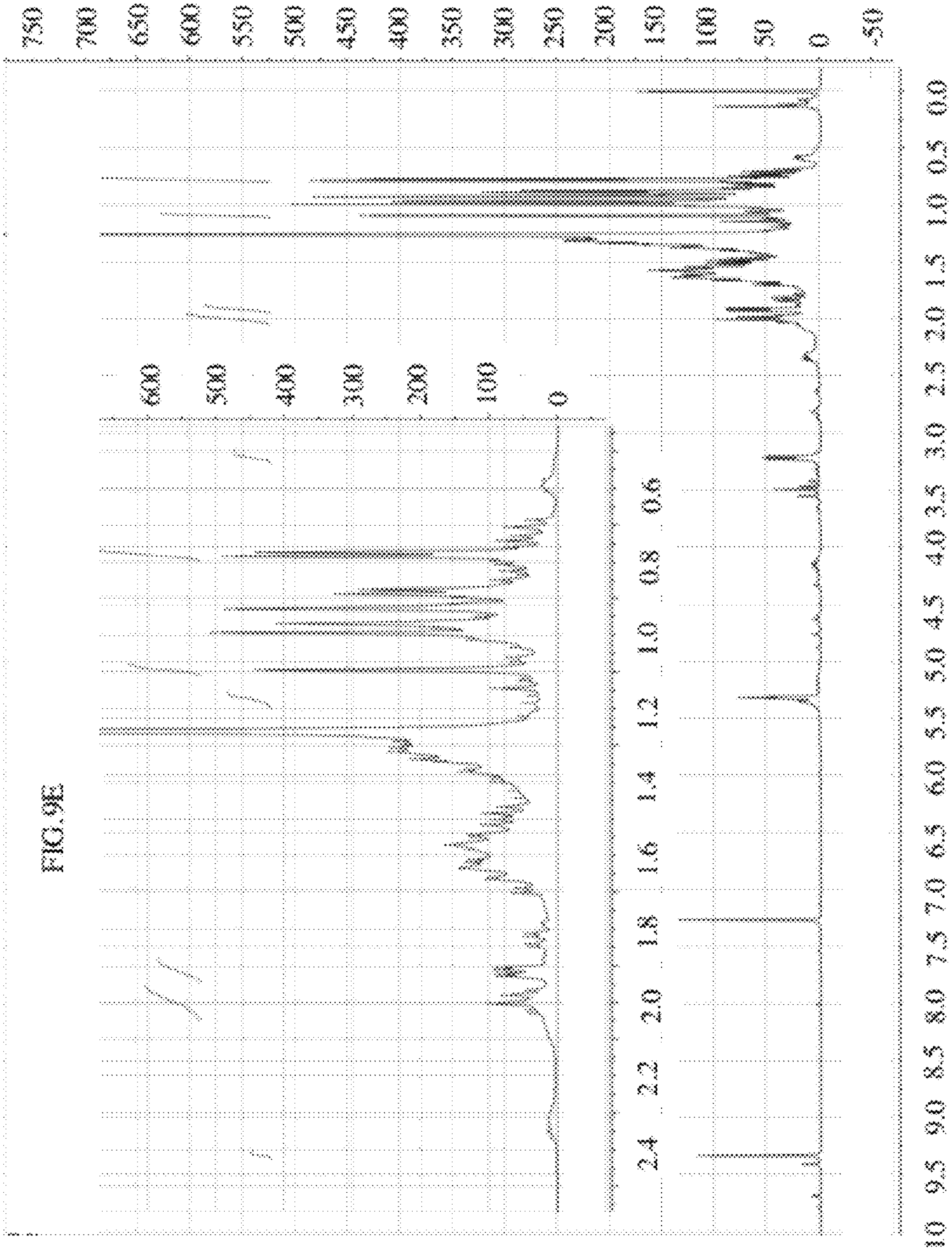
Figure 9F:
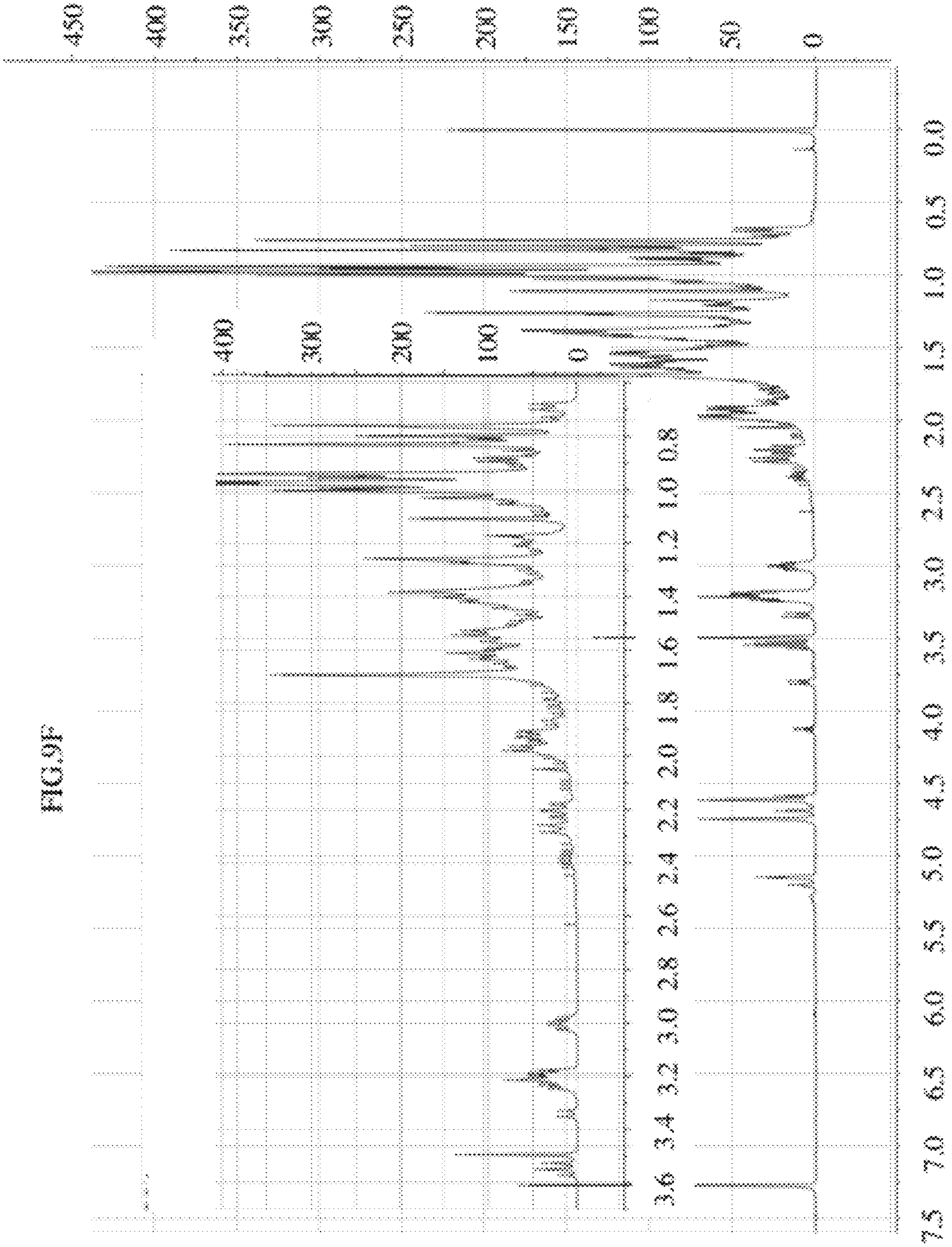
Figure 9G:
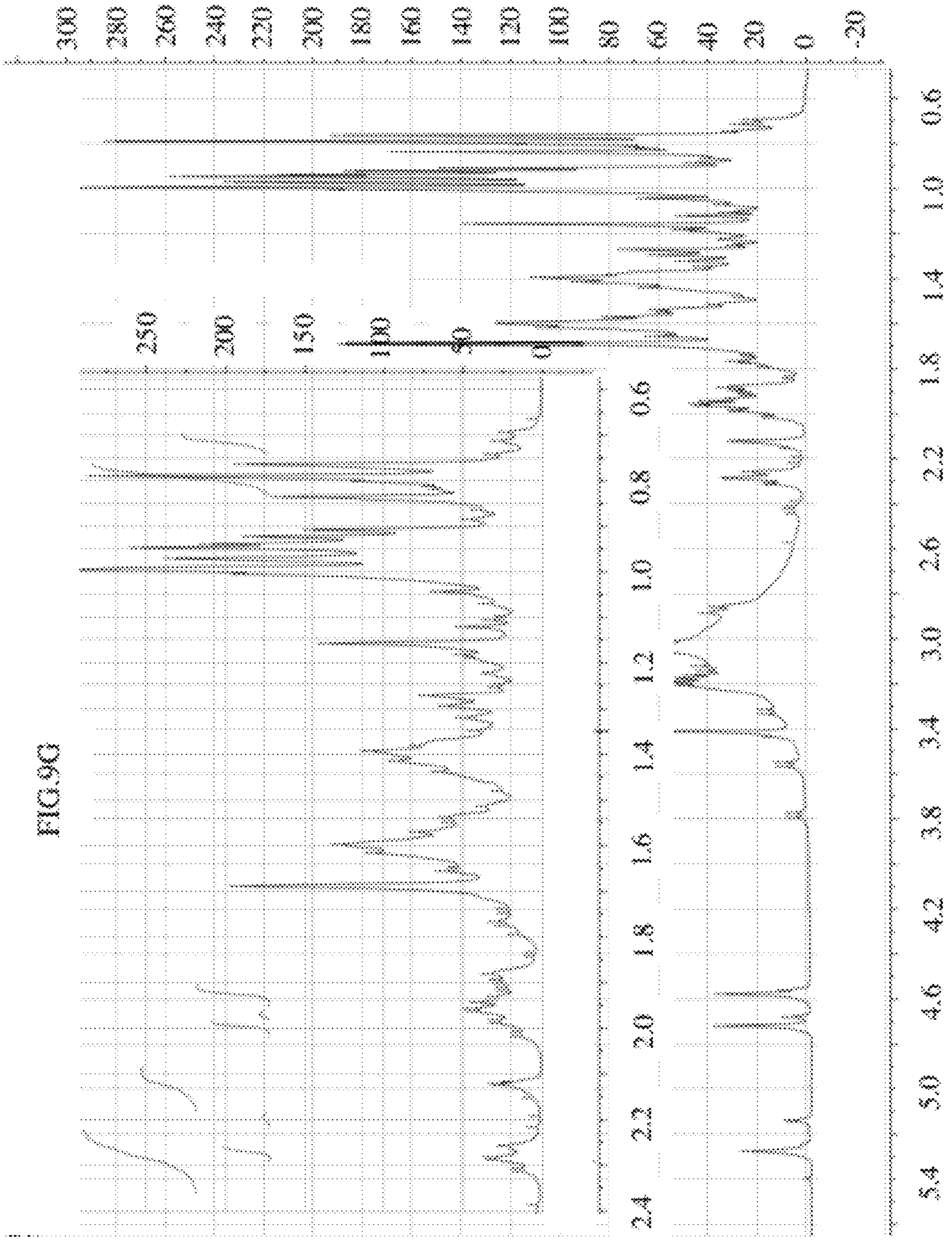
Figure 9H:
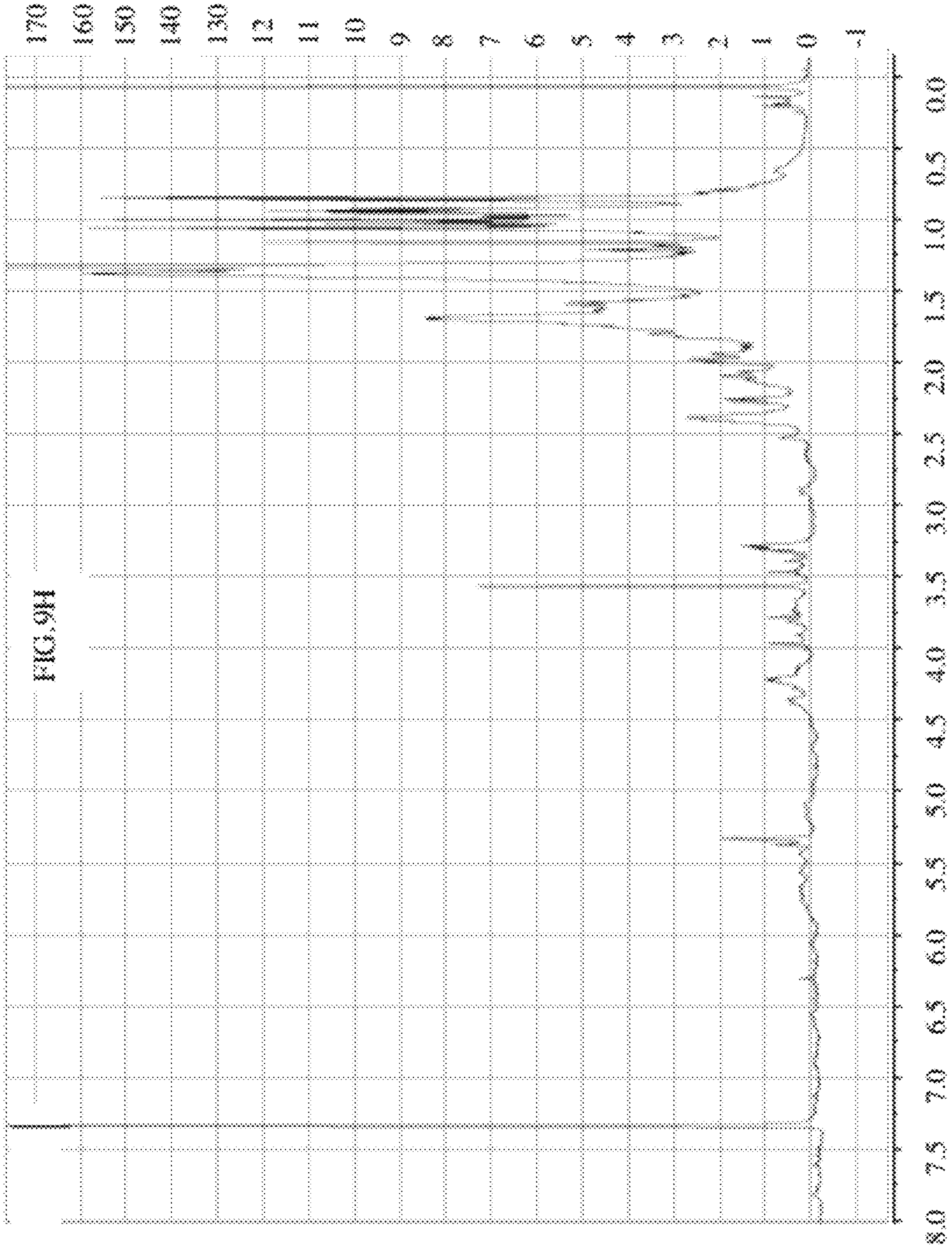
Figure 9I:
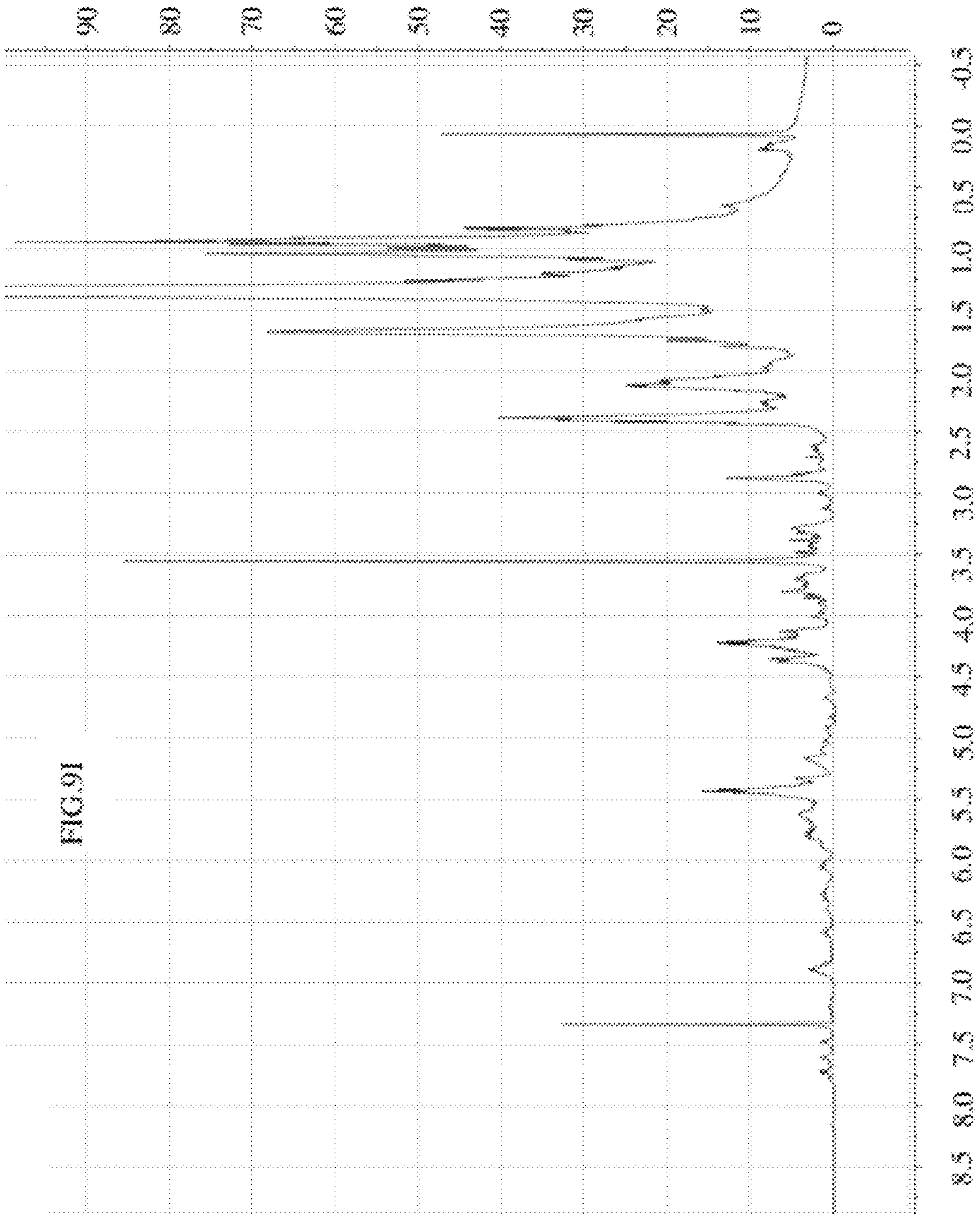

The HNMR of triterpene is characterized by 7 methyl signals at upfield, an olefinic proton at ca. 5.3 ppm, and an oxygenated methine signal at ca 3.4 ppm along with many methylene and methine proton signals at upfield (ca. 1.0~2.5 ppm). The HNMR spectra (FIGS. 9B-9I) indicated the major components as steroids and triterpenes. No signals for significant quantity of glycosides were observed. No signals for α,β-unsaturated γ- or δ-lactones, which are characteristic for cardiac glycosides, were observed, suggesting that there is no cardiac glycoside or its aglycone existing in the Fr-O-4 fraction. The HNMR spectrum in FIG. 9C corresponds to a sub-fraction comprising at least one steroid and at least one or at least two different triterpene. The HNMR spectrum in FIG. 9B corresponds to a sub-fraction comprising at least two different tripenes, such as a mixture of two ursanes, and excluding a steroid.

Accordingly, the fraction O-4 comprises at least one triterpene and at least one steroid. In some embodiments, the fraction O-4 comprises at least two different triterpenes and at least two different steroids, or the fraction comprises plural different triterpenes and plural different steroids. The O-4 fraction evaluated in this example excludes a therapeutically effective amount of cardiac glycoside. In some embodiments, the fraction O-4 excludes a cardiac glycoside. In some embodiments, a first sub-fraction of the fraction O-4 comprises at least one steroid and at least one triterpene or at least two different triterpenes, a second sub-fraction comprises at least two different tripenes and excludes a steroid. In some embodiments, each of the first and second sub-fractions excludes cardiac glycoside.

The fraction O-4 was tested in OGD treated brain slices (stroke model) and non-OGD treated (i.e. control) brain slices (non-stroke model). The data indicate that the extract O-4 fraction provides substantial neuroprotection when using solutions of extract O-4 fraction ranging in concentration from 100 ng/mL to 1 μg/ml and provides even greater neuroprotection when using solutions of extract O-4 fraction ranging in concentration from 1 μg/mL to 1 mg/mL. Accordingly, a liquid dosage form containing 100 ng/mL to 1 mg/mL of a fraction of extract per mL of liquid dosage form should provide neuroprotection in a subject to which it is administered.

While no direct measurements have been made in human brain following a systemic dose of the extract, it is assumed that one or more pharmacologically active components in the fraction of extract will cross the blood brain barrier when administered to a subject. Oleandrin as pure compound or contained within the SCF extract known as PBI-05204 has been shown in a rodent (mice) model to effectively cross the blood brain barrier and enter into the brain. It is reasonable to expect that oleandrin would do the same with regard to a human blood brain barrier.

Accordingly, the invention provides a method of protecting neurons against loss of activity caused by oxygen depletion or oxygen-glucose depletion by exposing the oxygen depleted and/or glucose-depleted neurons to an effective amount of *Nerium* species or *Thevetia* species extract to minimize loss of activity, reduce the rate of loss of activity, stop the loss of activity, slow down onset of loss of activity, and/or protect the function of neurons caused by exposing the oxygen depleted and/or glucose-depleted conditions. In some embodiments, the method employs an effective amount of a fraction or sub-fraction of *Nerium* species extract or *Thevetia* species extract. In some embodiments, the fraction or sub-fraction has been prepared by liquid chromatography fractionation of the extract. In some embodiments, the fraction excludes a cardiac glycoside, and in other embodiments, the fraction or sub-fraction includes one or more cardiac glycosides, in particular of those described herein.

Figure 2A:
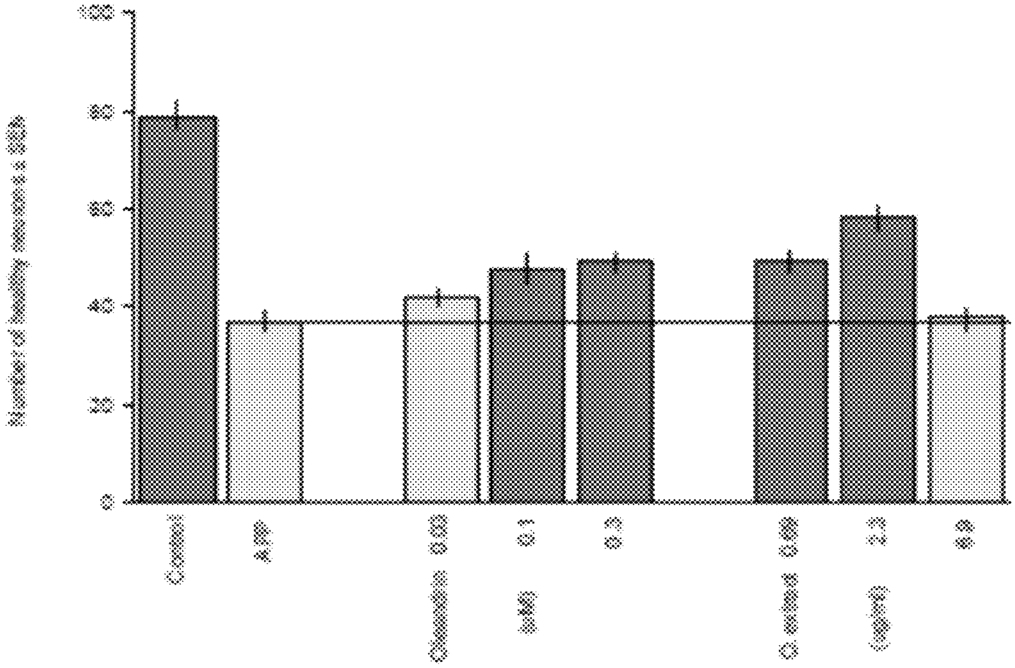
FIGS. 2A-2C depict results of the comparative evaluation of oleandrin versus the unfractionated SCF extract of *Nerium oleander* in a neuroprotection brain-slice-based "Alzheimer's" assay (Example 9), wherein the number of healthy cortical neurons is determined following APP/Aβ-induced degeneration in the absence or presence of varying amount of those agents.
Figure 2B:
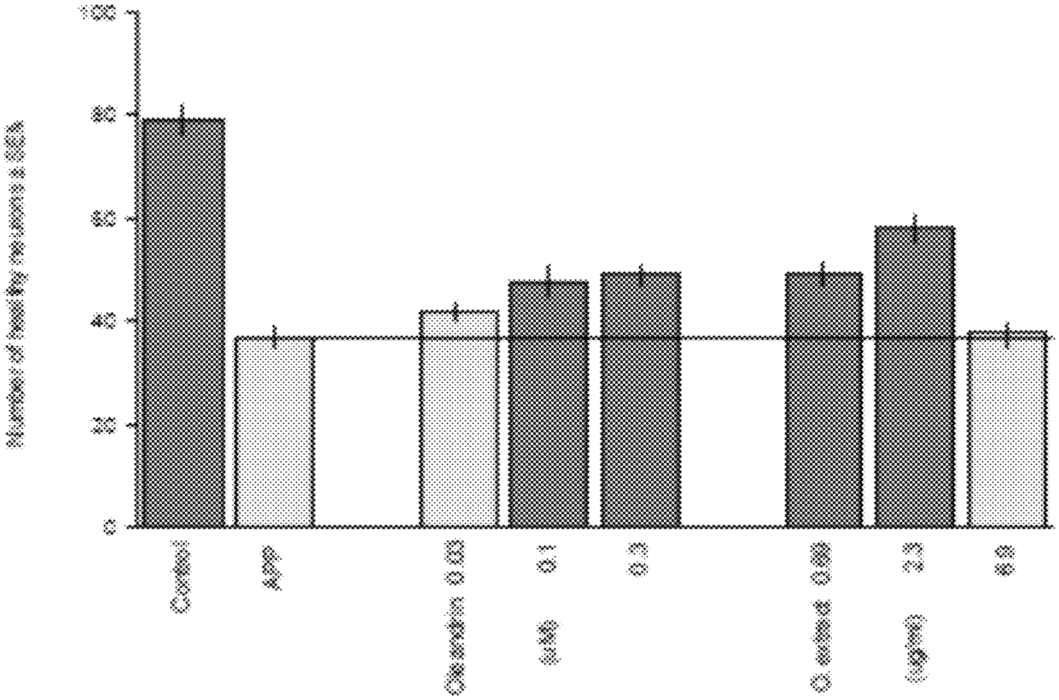
Figure 2C:
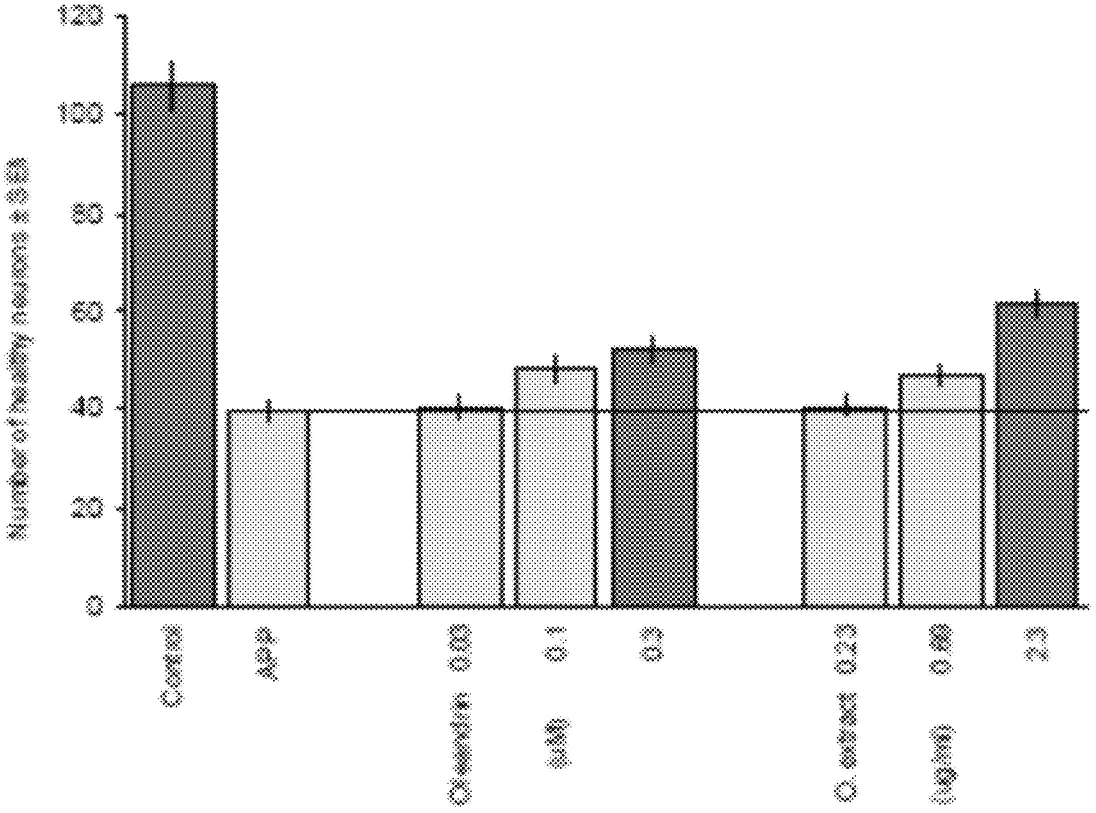
Figure 3A:
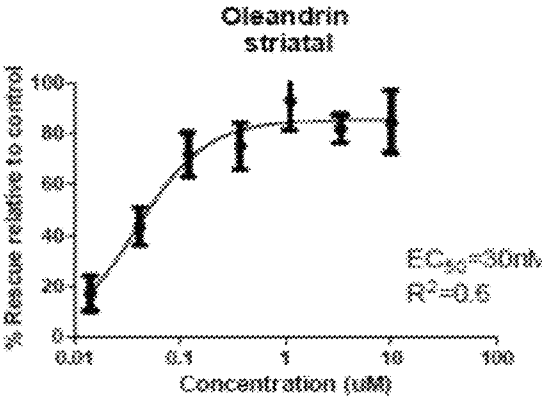
FIGS. 3A-3D depict results from duplicate experiments of the comparative evaluation of oleandrin (FIGS. 3A-3B) (FIGS. 3C-3D) in a neuroprotection cortico-striatal co-culture neuron-based "Huntington's disease" assay (Example 10), wherein the percent rescue, relative to control, of cortical neurons versus striatal neurons transfected with a mutant form of the Huntington (htt) protein is determined in the absence or presence of varying amounts of oleandrin.
Figure 3B:
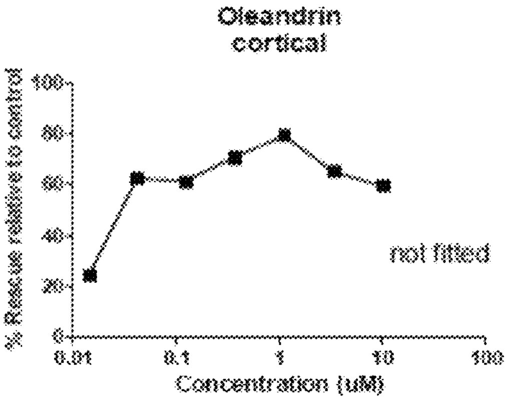
Figure 3C:
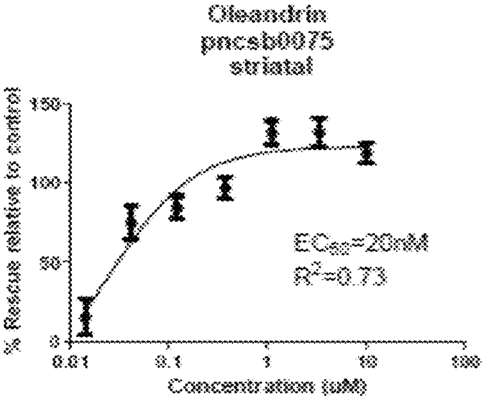
Figure 3D:
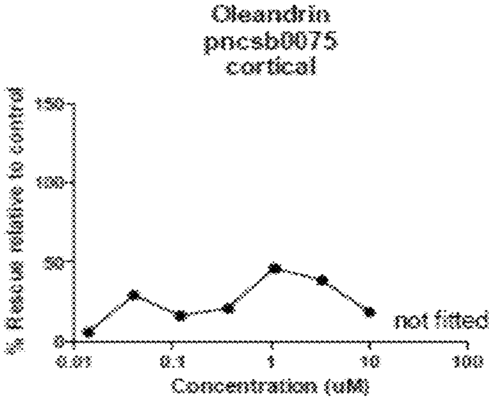

Example 9 provides a detailed description of an in vitro assay used to evaluate the efficacy of the extract for the treatment of Alzheimer's disease. The assay is a brain slice-based assay for APP/Aβ-induced (APP: amyloid precursor protein) degeneration of cortical pyramidal neurons. Upon cleavage by a secretase enzyme, the APP is reduced to Aβ peptides which are believed to be a causative factor in beta-amyloid plaque formation. Aβ proteins are associated with beta-amyloid plaque formation and are believed to be a hallmark if not etiologic factor in Alzheimer's disease. Biolistic transfection is used to introduce vital markers such as YFP (a marker yellow fluorescent protein) and to introduce disease gene constructs into the same neuronal populations in the brain slices. YFP is co-transfected with APP isoforms leading to the progressive degeneration of cortical pyramidal neurons over the course of three to four days after brain slice preparation and transfection. The data (FIGS. 2A-2C) indicate that the *Nerium* species SCF extract provided a concentration-dependent neuroprotection to APP-transfected brain slices thereby rescuing levels nearly to the same levels as provided by BACE inhibitor drugs, i.e. beta secretase inhibtor drugs. The beta secretase enzyme cleaves the APP precursor protein into toxic Aβ-proteins. The oleandrin-containing SCF extract appeared to provide greater neuroprotection than oleandrin alone. The data in FIGS. 2A-2C are of significance in that few compounds or therapeutic strategies in the literature have shown any significant protection of neurons in this in vitro assay representative of Alzheimer disease.

Figure 6:
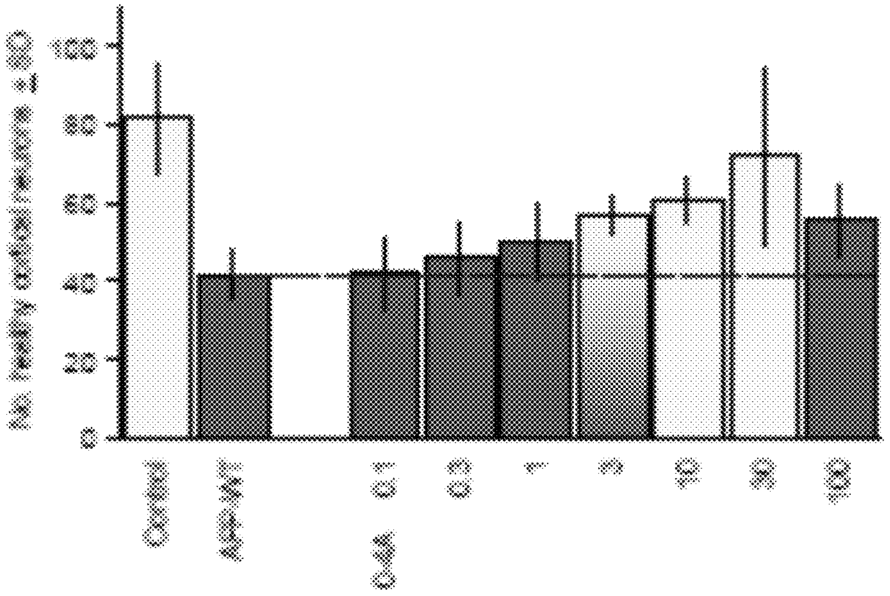
FIG. 6 depicts the results of the comparative evaluation of a fraction (O-4 or O-4A) of *Nerium oleander* SCF extract versus untreated (cells were not transfected with APP/Aβ) in an APP-based "Alzheimer's" assay (Example 11), wherein the number of healthy cortical neurons is determined following APP/Aβ-induced degeneration in the absence or presence of varying amount of those agents.

The APP-WT brain slice-based Alzheimer's assay was repeated (Example 11) using fractions of the SCF extract of *Nerium oleander*. The number of healthy cortical neurons was determined following APP/Aβ-induced degeneration in the presence of varying amounts of fraction O-4A of the SCF extract (0.01 to 100 μg/ml). Exposure to oxygen and glucose deprivation served as the internal positive control producing the stroke-like mediated injury to neurons. The negative control was simply the relative health of the brain slice neurons without OGD treatment or exposure to treatments. The data is depicted in FIG. 6, wherein the lighter colored bars indicate a significant difference with respect to the APP-WT condition by ANOVA followed by Dunnett's post hoc comparison test at the 0.05 confidence level. The data indicate that the O-4A fraction provides neuroprotection in this assay, even though it does not contain any cardiac glycosides.

Figure 7:
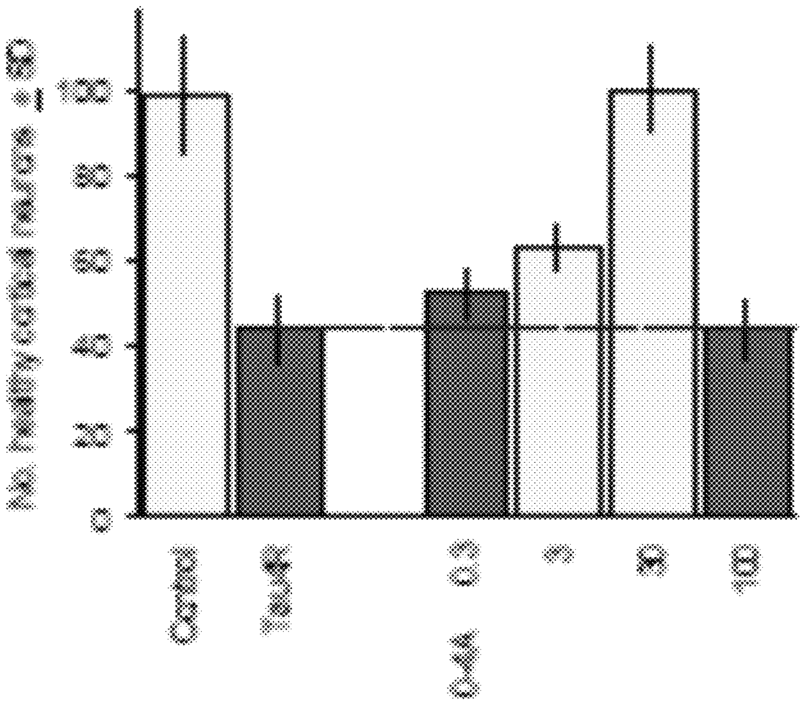
FIG. 7 depicts the results of the comparative evaluation of a fraction (O-4) of *Nerium oleander* SCF extract versus untreated (cells were not transfected with APP/Aβ) in a Tau4R based "Alzheimer's" assay (Example 12), wherein the number of healthy and damaged cortical neurons are determined following Tau4R in the absence or presence of varying amounts of those agents.
Figure 8A:
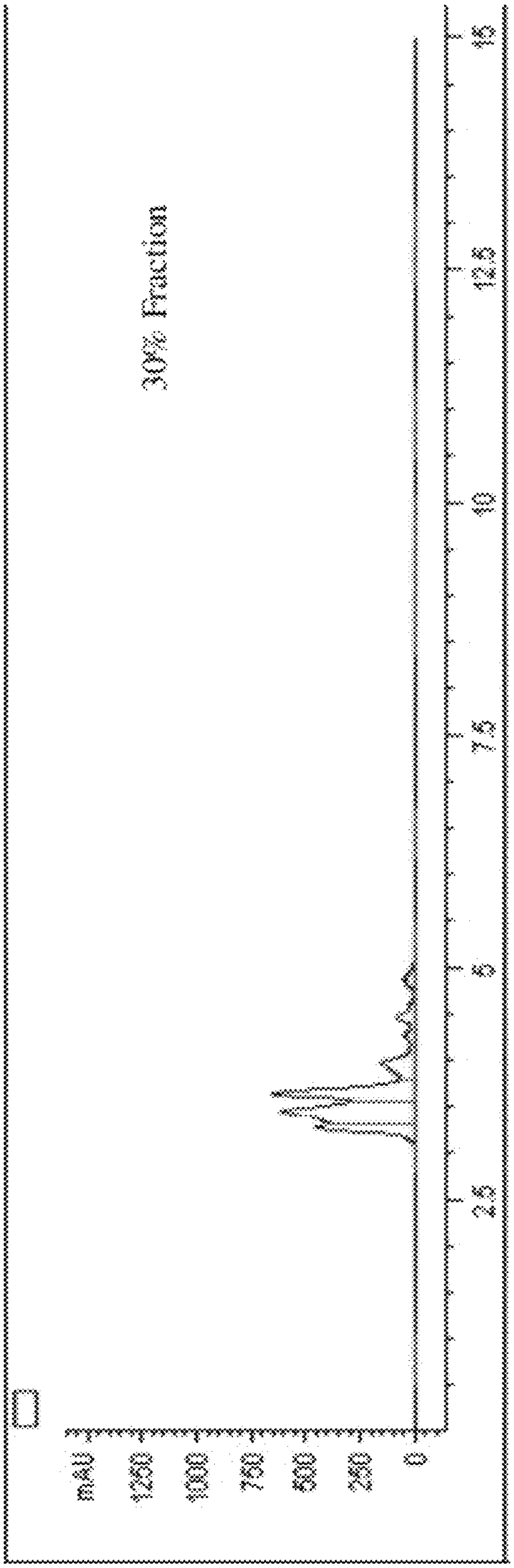
FIGS. 8A-8D depict the chromatograms obtained by HPLC analysis of the fractions prepared according to Example 13.
Figure 8B:
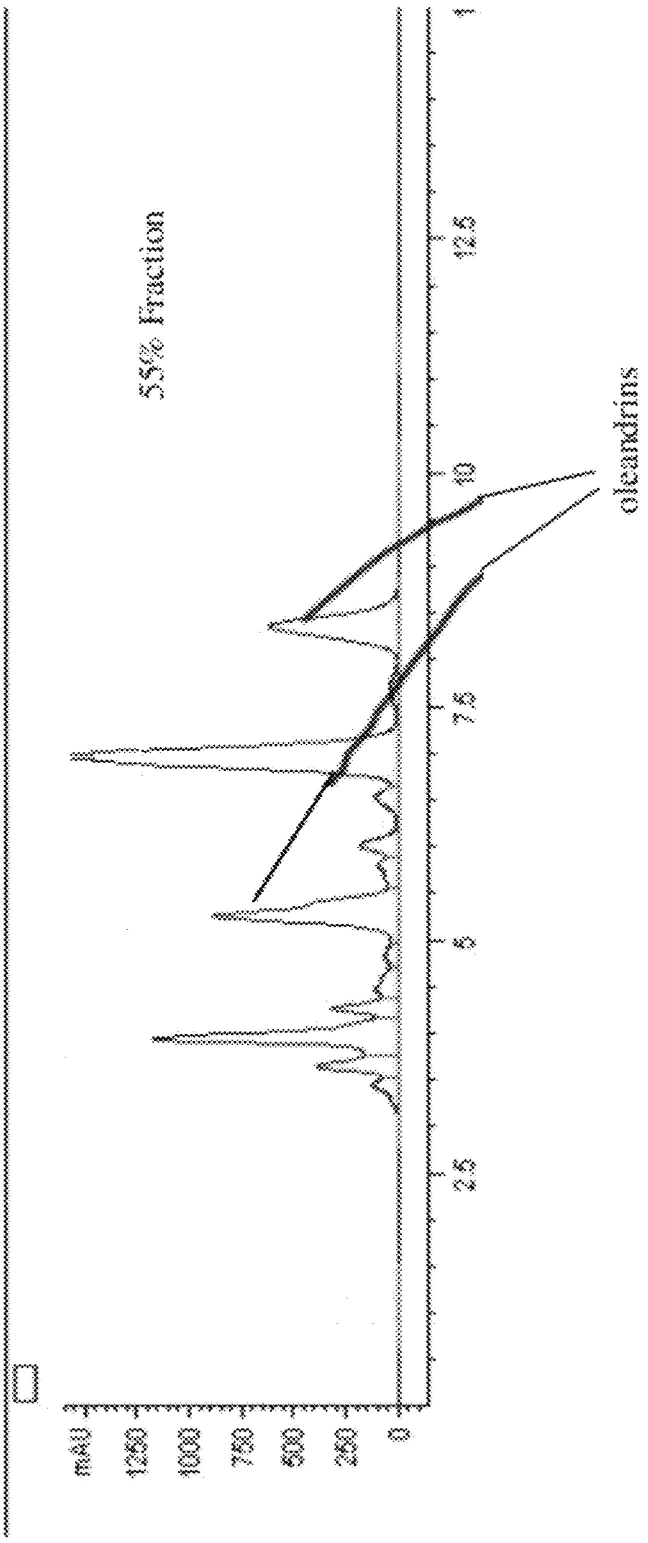
Figure 8C:
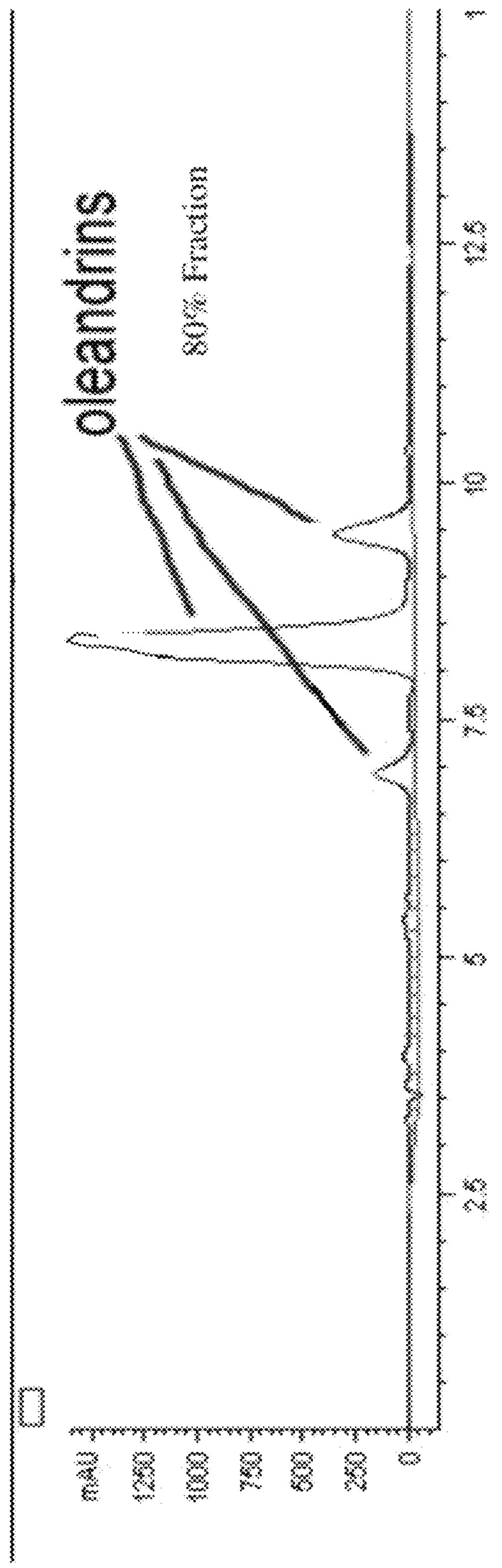
Figure 8D:
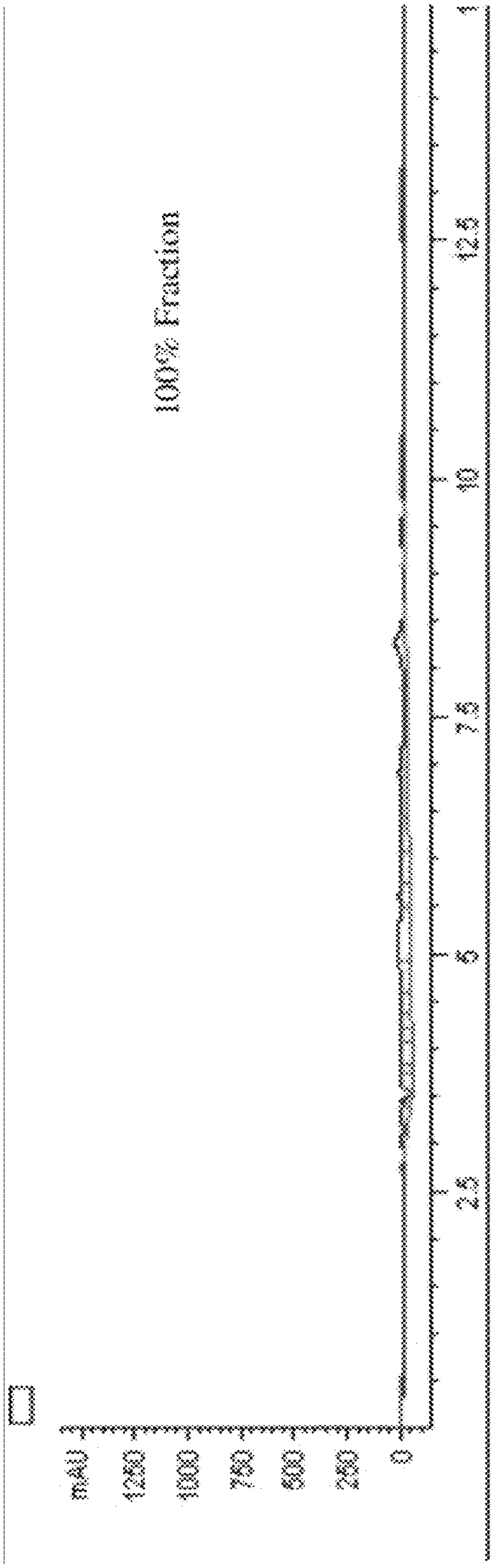

Fraction O-4 (O-4A) of the SCF extract of *Thevetia* oleander was evaluated with the tau4R brain slice-based Alzheimer's assay (Example 12). The number of healthy cortical neurons is determined. Efficacy in this assay is defined as or based upon the relative total number of healthy versus unhealthy number and percentage of degraded neurons in the presence of varying amounts of fraction O-4A of the SCF extract (0.3 to 100 μg/ml, the concentration having been determined by weight of the extract). The negative control in these experiments consisted of brain slices that were not exposed to OGD while brain slices exposed to OGD but not treated with fractions derived from unfractionated *Nerium oleander* extract served as the internal positive control. The data is depicted in FIG. 7, wherein the lighter colored bars indicate a significant difference with respect to damaged neurons by ANOVA followed by Dunnett's post hoc comparison test at the 0.05 confidence level. The data indicate that the O-4A fraction provides neuroprotection in this assay, even though it does not contain cardiac glycoside.

Accordingly, the invention provides a method of protecting neurons against loss of activity caused by Alzheimer's disease, the method comprising: exposing the neurons exhibiting characteristics of Alzheimer's disease to an effective amount of extract of *Nerium* species or of *Thevetia* species to minimize loss of activity, reduce the rate of loss of activity, stop the loss of activity, slow down onset of loss of activity, and/or critical functioning of the neurons caused by Alzheimer's disease. In some embodiments, the method employs an effective amount of a fraction of *Nerium* species extract or *Thevetia* species extract. In some embodiments, the fraction has been prepared by liquid chromatography fractionation of the extract. In some embodiments, the fraction excludes a cardiac glycoside, and in other embodiments, the fraction includes one or more cardiac glycosides, in particular of those described herein.

Example 10 provides a detailed description of an assay used to evaluate the efficacy of the extract for the treatment of Huntington's disease. Mutant htt protein is introduced via electroporation into high-density, mixed co-cultures of cortical neurons, striatal neurons, and glia. The striatal and cortical neurons are transfected with different color fluorescent proteins thereby facilitating the separate identification of the different types of neurons in the co-culture. The color fluorescent proteins are fluorescent and 'emit' color upon activation with a light source of appropriate wavelength. The data (FIGS. 3A-3D) indicate that oleandrin and the SCF extract of *Nerium oleander* are more effective than KW6002 (an adenosine 2a receptor antagonist) in terms of providing a greater number of surviving neurons. The data also indicate that the SCF extract is more effective than oleandrin alone, suggesting that the extract further comprises one or more therapeutically effective agents, aside from oleandrin, that can be used to treat Huntington's disease. Such other agents can be used along with or in the absence of oleandrin or other cardiac glycoside. Accordingly, the invention provides a method of protecting neurons against loss of activity caused by Huntington's disease, the method comprising: exposing the neurons exhibiting characteristics of Huntington's disease to an effective amount of oleandrin or oleandrin-containing extract to minimize loss of activity, reduce the rate of loss of activity, stop the loss of activity, slow down onset of loss of activity, and/or normal function of the neurons caused by Huntington's disease.

Example 16 details an exemplary brain-slice assay that can be used to evaluate the efficacy of extract in the treatment of stroke in a subject following completion of a delay period after the stroke. The brain-slice assay with oxygen glucose deprivation is conducted as described herein; however, rather than treating the brain slices prophylactically with the extract, they were treated with the extract after delay periods of 0, 1, 2, 4, and 6 hours. The data should demonstrate that the extract containing is effective at providing significant neuroprotection for delay periods of up to 1, up to 2, up to 3, up to 4, up to 5, up to about 6 hours after the stroke.

Accordingly, the invention provides a time-delayed method of treating stroke in a subject by administration of a dose of extract of *Nerium* species or of *Thevetia* species to a subject after the subject has suffered a stroke. Within an acceptable delay period after a subject has suffered the stroke, an initial dose of the extract is administered according to an initial dosing regimen. Then, adequacy of the subject's clinical response and/or therapeutic response to treatment with the extract is determined. If the subject's clinical response and/or therapeutic response is adequate, then treatment with the extract is continued as needed until the desired clinical endpoint is achieved. Alternatively, if the subject's clinical response and/or therapeutic response are inadequate at the initial dose and initial dosing regimen, the dose is escalated or deescalated until the desired clinical response and/or therapeutic response in the subject is achieved. Dose escalation or de-escalation can be performed in conjunction with a change in the dosing regimen, such as a change in dosing frequency or overall period of dose administration.

Some of the brain slice assays herein are conducted under conditions wherein the brain tissue is treated with the extract prior to OGD. Under those conditions, the data establishes the utility of the extract at prophylactically providing neuroprotection against damage caused by stroke.

If a clinician intends to treat a subject having a neurological condition with a combination of extract, or composition thereof, and one or more other therapeutic agents, and it is known that the particular neurological condition, which the subject has, is at least partially therapeutically responsive to treatment with said one or more other therapeutic agents, then the present method invention comprises: administering to the subject in need thereof a therapeutically relevant dose of extract (or a fraction or sub-fraction thereof) and a therapeutically relevant dose of said one or more other therapeutic agents, wherein the extract (or a fraction or sub-fraction thereof) is administered according to a first dosing regimen and the one or more other therapeutic agents is administered according to a second dosing regimen. In some embodiments, the first and second dosing regimens are the same. In some embodiments, the first and second dosing regimens are different.

If the neurological condition being treated is Alzheimer's disease, the one or more other therapeutic agents can be selected from the group consisting of BACE inhibitors or acetylcholinesterase inhibitors. In some embodiments, the one or more other therapeutic agents can be selected from the group consisting of Namenda™ (memantine HCl), Aricept™ (donepezil), Razadyne™ (galantamine), Exelon™ (rivastigmine), and Cognex™ (tacrine).

If the neurological condition being treated is Huntington's disease, the one or more other therapeutic agents can be selected from the group consisting of natural products, anticonvulsants, NMDA (n-methyl d-aspartate) receptor antagonists, and sodium channel blockers. Exemplary agents include Vitamin E, Baclofen (a derivative of CoQ10), Lamotrigine (an anticonvulsant), remacemide (an anesthetic which is a low affinity NMDA antagonist), and riluzole (Na channel blocker). The efficacy of each of these agents is considered to be low (Mestre T. et al, Chochrane Database Systematic Reviews Jul. 8, 2009; 8(3): CD006455) on its own; however, it is expected that administration of a dosage form containing extract to subjects receiving one or more of these other agents will provide a subject, having a neurological disorder, an improved clinical affect as compared to administration of these agents absent the extract.

If the neurological condition being treated is stroke-mediated ischemic brain injury (ischemic stroke), then the therapeutic treatments disclosed in the literature (Gutierrez M. et al. "Cerebral protection, brain repair, plasticity and cell therapy in ischemic stroke" *Cerebrovasc. Dis.* 2009; 27 Suppl 1:177-186), e.g. intravenous thrombolysis, can be employed in addition to the extract. In some embodiments, the one or more other therapeutic agents can be selected from the group consisting of drugs such as Alteplase (a thrombolytic agent).

The one or more other therapeutic agents can be administered at doses and according to dosing regimens that are clinician-recognized as being therapeutically effective or at doses that are clinician-recognized as being sub-therapeutically effective. The clinical benefit and/or therapeutic effect provided by administration of a combination of the extract and one or more other therapeutic can be additive or synergistic, such level of benefit or effect being determined by comparison of administration of the combination to administration of the individual extract and one or more other therapeutic agents. The one or more other therapeutic agents can be administered at doses and according to dosing regimens as suggested or described by the U.S. Food and Drug Administration (U.S.F.D.A.), World Health Organization (W.H.O), European Medicines Agency (E.M.E.A.), Therapeutic Goods Administration (TGA, Australia), Pan American Health Organization (PAHO), Medicines and Medical Devices Safety Authority (Medsafe, New Zealand) or the various Ministries of Health worldwide.

If a cardiac glycoside is used according to the invention, it can be any cardiac glycoside known to possess Na,K-ATPase binding activity. The cardiac glycoside should be capable of crossing the blood-brain barrier and being retained in brain tissue for an extended period of time following administration. In this regard, the cardiac glycoside should be retained in the brain for at least 8 hours following administration of the cardiac glycoside due to tissue binding and a consequent low clearance rate.

If present, the cardiac glycoside can be present in pure form or as a mixture with one or more other compounds. The cardiac glycoside can be present as an extract.

The extract can be prepared by supercritical fluid (SCF) carbon dioxide ($CO_2$) extraction or a chemically modified form of such an extract (e.g. an extract that includes ethanol or was made using SCF $CO_2$ and ethanol; Example 1). The extract can be obtained by extraction of plant material with an organic solvent, e.g. ethanol, methanol, propanol or other such solvents. The extract can be obtained from plant material. The plant material can be plant mass such as obtained from *Nerium* species, such as *Nerium* oleander, or of *Thevetia* species, such as *Thevetia neriifolia* or *Thevetia peruviana* (otherwise known as yellow oleander). The extraction process can be conducted on a dried powder of *Nerium oleander* leaves prepared according to a process described in a currently-pending U.S. provisional application Ser. No. 60/653,210 filed Feb. 15, 2005 in the name of Addington or U.S. application Ser. No. 11/340,016 filed Jan. 26, 2006 in the name of Addington, U.S. application Ser. No. 11/191,650 filed Jul. 28, 2006 (now U.S. Pat. No. 7,402,325 issued Jul. 22, 2008) in the name of Addington, or PCT International Patent Application No. PCT/US06/29061 filed Jul. 26, 2006, or Newman et al. (*Mol. Interven.* (2008), 8, 36-49), the entire disclosures of which are hereby incorporated by reference, or by a process described herein. These methods can also be used to prepare the unfractionated extract of *Nerium* species or of *Thevetia* species. Unless otherwise specified, the term "extract" as used herein can be taken to mean the "unfractionated extract" or a fraction of the extract or a sub-fraction of a fraction of the extract. The term "unfractionated extract" is generally taken to mean an extract obtained by extraction of plant material, wherein the extract has not been subjected to fractionation, such as fractionation or separation into individual components or groups of components by chromatography or solvent extraction, following initial preparation of the extract.

As used herein, the term "oleandrin" is taken to mean all known forms of oleandrin unless otherwise specified. Oleandrin can be present in racemic, optically pure or optically enriched form. *Nerium oleander* plant material can be obtained, for example, from commercial plant suppliers such as Aldridge Nursery, Atascosa, Tex.

The unfractionated extract can be obtained by modified (e.g. ethanol) or unmodified supercritical fluid extraction of a cardiac glycoside-containing plant mass, e.g. of a *Nerium* species or *Thevetia* species containing plant mass. The supercritical fluid extract can comprise one or more pharmacologically active agents, extracted from the plant mass, that contributes to the therapeutic efficacy of the extract when administered to a subject. When two or more such agents are present, they can contribute additively or synergistically to the therapeutic efficacy of the extract.

The unfractionated extract can be prepared by various different processes. The extract can be prepared as above or according to the process developed by Dr. Huseyin Ziya Ozel (U.S. Pat. No. 5,135,745) describes a hot-water extraction procedure for the preparation of the extract of the plant in water. The aqueous extract reportedly contains several polysaccharides with molecular weights varying from 2 KD to 30 KD, oleandrin and oleandrigenin, odoroside and neritaloside. The polysaccharides reportedly include acidic homopolygalacturonans or arabinogalaturonans. U.S. Pat. No. 5,869,060 to Selvaraj et al. discloses hot water extracts of *Nerium* species and methods of production thereof, e.g. Example 2. The resultant extract can then be lyophilized to produce a powder. U.S. Pat. No. 6,565,897 (U.S. Pregrant Publication No. 20020114852 and PCT International Publication No. WO 2000/016793 to Selvaraj et al.) discloses a hot-water extraction process for the preparation of a substantially sterile extract. Erdemoglu et al. (*J. Ethnopharmacol.* (2003) Nov. 89(1), 123-129) discloses results for the comparison of aqueous and ethanolic extracts of plants, including *Nerium oleander*, based upon their anti-nociceptive and anti-inflammatory activities. Organic solvent extracts of *Nerium* oleander are disclosed by Adome et al. (*Afr. Health Sci.* (2003) Aug. 3(2), 77-86; ethanolic extract), el-Shazly et al. (*J. Egypt Soc. Parasitol.* (1996), Aug. 26(2), 461-473; ethanolic extract), Begum et al. (*Phytochemistry* (1999) Feb. 50(3), 435-438; methanolic extract), Zia et al. (*J. Ethnolpharmacol.* (1995) Nov. 49(1), 33-39; methanolic extract), and Vlasenko et al. (*Farmatsiia.* (1972) September.-October 21(5), 46-47; alcoholic extract). U.S. Pregrant Patent Application Publication No. 20040247660 to Singh et al. discloses the preparation of a protein stabilized liposomal formulation of oleandrin for use in the treatment of cancer. U.S. Pregrant Patent Application Publication No. 20050026849 to Singh et al. discloses a water soluble formulation of oleandrin containing a cyclodextrin. U.S. Pregrant Patent Application Publication No. 20040082521 to Singh et al. discloses the preparation of protein stabilized nanoparticle formulations of oleandrin from the hot-water extract.

The SCF extraction can be conducted in the presence of a modifier in the supercritical fluid, such as alcohol, e.g. ethanol, to enhance extraction of the desired compound(s) from the plant mass (PCT/US06/29061 filed Jul. 26, 2005; U.S. Pat. No. 7,402,325; and U.S. Ser. No. 12/019,435 filed Jan. 24, 2008, or Newman et al. (*Mol. Interven.* (2008), 8, 36-49), the entire disclosures of which are hereby incorporated by reference). Modifiers generally possess volatility between that of the supercritical fluid and of the compound being extracted, and they must be miscible with the supercritical fluid. In some embodiments, the modifier is a liquid at ambient conditions. By way of example and without limitation, a modifier can be selected from the group consisting of ethanol, methanol, propanol, acetone, ethyl acetate, methylene chloride, etc.

It is possible that the extracts also differ in their relative performance as determined by efficacy in the assays included herein. Even so, if the one or more pharmacologically active agents is present in a sufficiently high amount or concentration in the extract to be able to prepare a therapeutically relevant dose, then the extract is considered part of the invention.

Example 13 describes a chromatographic method for fractionating an SCF extract into five different fractions: O—H, O-2, O-3, O-4 and O-5. The fractions were prepared by loading the unfractionated extract onto an ODS—silica gel column equilibrated with water and subsequently eluting different fractions of the extract by sequentially passing various portions of aqueous mobile phase varying in methanol content (30%, 55%, 80% and 100%) through the column, collecting the respective effluents (fractions) and concentrating the effluents by solvent evaporation under reduced pressure to remove the solvent, thereby providing the fractions O-1 (or O—H), O-2, O-3, O-4 and O-5. The fractions were analyzed according to Example 14 and their composition in terms of cardiac glycoside and other components was determined by thin layer chromatography using a sensitive dye indicator that adheres to (and hence is useful for detecting) cardiac glycosides. In addition, the presence or absence of cardiac glycosides in these fractions was analyzed using liquid chromatography/tandem mass spectrometry or DAD-UV detection.

A fraction or sub-fraction of the extract can be analyzed by liquid chromatography employing a stationary phase different than ODS-silica gel and/or by employing a mobile phase different than water. Exemplary suitable stationary phases are further described herein.

FIGS. 8A-8D depict the chromatograms obtained following HPLC analysis of the fractions Fr-O-1, Fr-O-2, Fr-O-3 and Fr-O-4 of Example 13. Based upon a comparison of retention times obtained using corresponding external reference samples, it was determined the (Fr-O-2 and Fr-O-3) fractions contain oleandrin derivatives (cardiac glycosides), oleandrin (Rt=8.3 min) and other unidentified components. The bulk of the oleandrin found in the original unfractionated SCF extract was mainly in the Fr-O-3 fraction. The Fr-O-4 contained no quantifiable amounts of any cardiac glycoside. Accordingly, the composition of the fractions differed according to the content of oleandrin, cardiac glycoside and other unidentified components.

| Fraction | Oleandrin (Y/N) | Other Cardiac Glycoside (Y/N) | Neuroprotection (Y/N) |
|---|---|---|---|
| O—H | N | N | Y |
| O-2 | N | Y | N |
| O-3 | Y | Y | Y |
| O-4 (O-4A) | N | N | Y |
| O-5 | N | N | N |

These fractions were then subjected to the neuroprotection brain slice-based assay detailed in Example 15 to determine the level of neuroprotection provided by each. The data are depicted in FIGS. 4A-4E, wherein the neuroprotective activity of an aqueous solution containing SCF extract (23 μg/ml) was compared to that of other solutions containing 0.03, 0.3 or 3 μg/ml of other component(s). All the fractions were weighed out and compared on an equal mass weight basis. It was determined that fractions (described herein) containing oleandrin, or cardiac glycoside, as well as some fractions not containing oleandrin, or cardiac glycoside, could provide neuroprotection.

Figure 5:
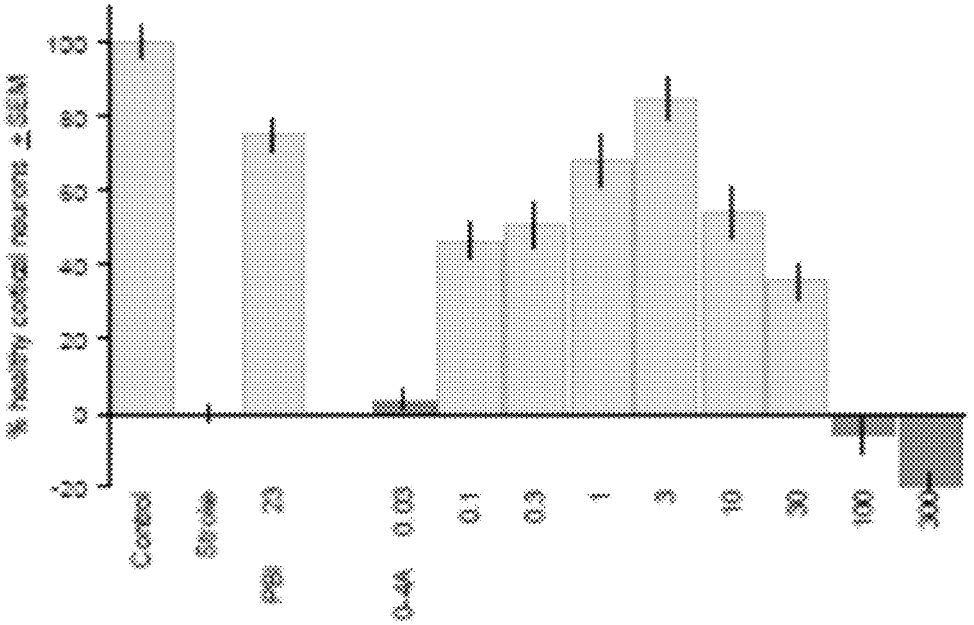
FIG. 5 depicts the results of a concentration-response brain-slice-based "stroke" assay (Example 15) for fraction O-4 of the SCF extract of *Nerium oleander* versus the parent unfractionated *Nerium oleander* SCF extract (PBI or PBI-05204).

Performance of fraction O-4 of the SCF extract in the brain sliced-based stroke assay (Example 15) was compared to that of the unfractionated SCF extract (PBI-05204). The performance of varying amounts (0.03 to 300 μg/ml) of the O-4 fraction was compared to a fixed amount (23 μg of oleandrin ml) of extract. The data (FIG. 5) clearly indicates that fraction O-4 of the SCF extract of *Nerium oleander* retains its efficacy even though it does not contain oleandrin or detectable amount of any other cardiac glycoside. The lighter colored bars in FIG. 5 indicate significant difference with respect to the stroke condition (set to 0) by ANOVA followed by Dunnett's post hoc comparison test at the 0.05 confidence level.

Accordingly, the invention provides plural therapeutic fractions of *Nerium* species or *Thevetia* species extract, the fractions being selected from the group consisting of: a) a fraction comprising one or more pharmacologically active agents and excluding oleandrin and other cardiac glycosides, wherein the fraction provides neuroprotection; b) a fraction comprising one or more pharmacologically active agents, oleandrin and one or more other cardiac glycosides, wherein the fraction provides neuroprotection; and c) a different fraction comprising one or more other pharmacologically active agents (different than those in a) above) and excluding oleandrin and other cardiac glycosides, wherein the fraction provides neuroprotection.

The invention also provides a method of fractionating an extract of *Nerium* species or *Thevetia* species in order to provide one or more therapeutically effective fractions thereof. The method comprises: a) providing an extract of *Nerium* species or *Thevetia* species; b) fractionating the extract to provide two or more different fractions of the extract, a first extract comprising one or more pharmacologically active agents, which is not a cardiac glycoside, and excluding cardiac glycoside, and a second extract comprising one or more pharmacologically active agents, which is not a cardiac glycoside, and one or more cardiac glycosides. In some embodiments, the fractionation is performed by liquid chromatography with a stationary phase and a mobile phase. In some embodiments, the stationary phase comprises a medium selected from the group consisting of "reverse phase" resin, an inert non-polar substance that achieves sufficient packing for use in chromatography, e.g. composed of short (C8 to C18) carbon chains bonded to silica, cyano-bonded silica or phenyl bonded silica, ion-exchange resins (cation or anion based), "normal phase" resin, e.g. silica or organic moieties with cyano and amino functional groups. In some embodiments, the mobile phase comprises a solvent selected from the group consisting of water, methanol, ethanol, acetonitrile, tetrahydrofuran, water based buffered solutions or mixtures thereof. In some embodiments, the mobile phase comprises aqueous methanol, wherein the content of methanol is increased sequentially from about 30% up to 100% and the stationary phase is ODS-silica gel. The chromatography can be conducted using gradient elution mobile phase, stepwise elution mobile phase or a fixed composition mobile phase.

A fraction of extract can be sub-fractionated to provide two or more different sub-fractions of a fraction of extract. Sub-fractionation can be carried out by liquid chromatography of the fraction. A suitable stationary phase for liquid chromatography can comprise silica gel or other resins such as ion-exchange media, alumina or nonbonded C18 material and a suitable mobile phase for liquid chromatography can comprise a combination of two or more organic solvents differing in polarity: a less polar organic solvent and a more polar organic solvent. A suitable polar organic solvent can be tetrahydrofuran, dichloromethane, ethyl acetate, acetone, dimethylformamide, acetonitrile, n-butanol, isopropanol, n-propanol, ethanol, methanol, acetic acid and water. A suitable non-polar organic solvent can be ethyl acetate pentane, cyclopentane, hexane, cyclohexane, benzene, toluene, 1,4-dioxane, chloroform or diethyl ether.

Buffering agents for use in buffered solutions include any of those already known in the art of liquid chromatography. Exemplary buffering agents include those containing phosphate, acetate, citrate, formate, phosphate, trifluoroacetic acid, chloroacetate, sulfonate, alkyl amine, TAE, TBE, ammonia, BuffAR, carbonate, HEPES, MES, thiocyanate, CAPS, CHES, guanidine, MOPS, PIPES, TRIS, sulfate, hydroxide, alkali metal halide, tricine, or amino acid ions or combinations thereof. One or more ion-pairing agents and/or one or more organic modifiers can also be included in the mobile phase.

Other types of chromatography that can be used to fractionate the extract include size exclusion chromatography, normal phase chromatography, ion exchange chromatography, hydrophobic interaction chromatography or combinations thereof. It is also possible to use combined forms of different types of chromatography. A stationary phase can include a medium that is a combination of two or more different media used for reverse phase, size exclusion, ion exchange or hydrophobic interaction chromatography, e.g. a combination of reverse phase stationary phase and size exclusion stationary phase, combination of reverse phase stationary phase and ion exchange stationary phase, or other such combinations or two, three or four different stationary phase media. The stationary phase medium can be porous, non-porous, surface porous, diffusive porous or totally porous.

The invention provides a method of fractionating an extract comprising: a) providing an extract of extract obtained from *Nerium* species or *Thevetia* species; b) fractionating the extract by column chromatography, with ODS-silica gel as stationary phase and aqueous methanol as mobile phase, to provide at least two different fractions: a first fraction comprising at least one cardiac glycoside and at least one non-cardiac glycoside pharmacologically active agent, and another fraction excluding cardiac glycoside and comprising at least one non-cardiac glycoside pharmacologically active agent; c1) sub-fractionating the other fraction of b) by column chromatography, with silica gel as stationary phase and a mixture of at least two organic solvents differing in polarity as mobile phase, to provide at least two different sub-fractions: a sub-fraction comprising one or more steroids and one or more tritepenes, and another sub-fraction comprising two or more different tripenes and excluding a steroid, wherein the sub-fractions exclude cardiac glycoside.

In some embodiments, the method further comprises: c2) sub-fractionating the first fraction of b) by column chromatography, with silica gel as stationary phase and a mixture of at least two organic solvents differing in polarity as mobile phase, to provide at least two different sub-fractions: a sub-fraction comprising one or more steroids and one or more tritepenes, and another sub-fraction comprising two or more different tripenes and excluding a steroid, wherein either one or both of the sub-fractions further comprises cardiac glycoside.

The extract, or fraction or sub-fraction thereof, can be formulated in any suitable pharmaceutically acceptable dosage form. Parenteral, otic, ophthalmic, nasal, inhalable, buccal, sublingual, enteral, topical, oral, peroral, and injectable dosage forms are particularly useful. Particular dosage forms include a solid or liquid dosage forms. Exemplary suitable dosage forms include tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid and other such dosage forms known to the artisan of ordinary skill in the pharmaceutical sciences.

The amount of extract, or fraction or sub-fraction thereof, incorporated in a dose of the invention will be at least one or more dosage forms and can be selected according to known principles of pharmacy. An effective amount or therapeutically relevant amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when, administered to a patient. The appreciable biological response may occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors.

The desired dose for oral administration is up to 5 dosage forms although as few as one and as many as ten dosage forms may be administered as a single dose. Exemplary dosage forms contain 0.1 to 5 mg of the SCF extract per dosage form, for a total 0.1 to 500 mg (1 to 10 dose levels) per dose. Doses will be administered according to dosing regimens that may be predetermined and/or tailored to achieve specific therapeutic response or clinical benefit in a subject.

For use in treatment of mammals, the extract, or fraction or sub-fraction thereof, can be included in a dosage form. Some embodiments of the dosage form are not enteric coated and release their charge of extract within a period of 0.5 to 1 hours or less. Some embodiments of the dosage form are enteric coated and release their charge of cardiac downstream of the stomach, such as from the jejunum, ileum, small intestine, and/or large intestine (colon). Enterically coated dosage forms will release the extract into the systemic circulation within 1-10 hr after oral administration.

It should be noted that a compound herein might possess one or more functions in the formulation of the invention. For example, a compound might serve as both a surfactant and a water miscible solvent or as both a surfactant and a water immiscible solvent.

A liquid composition can comprise one or more pharmaceutically acceptable liquid carriers. The liquid carrier can be an aqueous, non-aqueous, polar, non-polar, and/or organic carrier. Liquid carriers include, by way of example and without limitation, a water miscible solvent, water immiscible solvent, water, buffer and mixtures thereof.

As used herein, the terms "water soluble solvent" or "water miscible solvent", which terms are used interchangeably, refer to an organic liquid which does not form a biphasic mixture with water or is sufficiently soluble in water to provide an aqueous solvent mixture containing at least five percent of solvent without separation of liquid phases. The solvent is suitable for administration to humans or animals. Exemplary water soluble solvents include, by way of example and without limitation, PEG (poly(ethylene glycol)), PEG 400 (poly(ethylene glycol having an approximate molecular weight of about 400), ethanol, acetone, alkanol, alcohol, ether, propylene glycol, glycerin, triacetin, poly(propylene glycol), PVP (poly(vinyl pyrrolidone)), dimethylsulfoxide, N,N-dimethylformamide, formamide, N,N-dimethylacetamide, pyridine, propanol, N-methylacetamide, butanol, soluphor (2-pyrrolidone), pharmasolve (N-methyl-2-pyrrolidone).

As used herein, the terms "water insoluble solvent" or "water immiscible solvent", which terms are used interchangeably, refer to an organic liquid which forms a biphasic mixture with water or provides a phase separation when the concentration of solvent in water exceeds five percent. The solvent is suitable for administration to humans or animals. Exemplary water insoluble solvents include, by way of example and without limitation, medium/long chain triglycerides, oil, castor oil, corn oil, vitamin E, vitamin E derivative, oleic acid, fatty acid, olive oil, softisan 645 (Diglyceryl Caprylate/Caprate/Stearate/Hydroxy stearate adipate), miglyol, captex (Captex 350: Glyceryl Tricaprylate/Caprate/Laurate triglyceride; Captex 355: Glyceryl Tricaprylate/Caprate triglyceride; Captex 355 EP/NF: Glyceryl Tricaprylate/Caprate medium chain triglyceride).

Suitable solvents are listed in the "International Conference on Harmonisation of Technical Requirements for Registration of Pharmaceuticals for Human Use (ICH) guidance for industry *Q3C Impurities: Residual Solvents*" (1997), which makes recommendations as to what amounts of residual solvents are considered safe in pharmaceuticals.

Exemplary solvents are listed as class 2 or class 3 solvents. Class 3 solvents include, for example, acetic acid, acetone, anisole, 1-butanol, 2-butanol, butyl acetate, tert-butlymethyl ether, cumene, ethanol, ethyl ether, ethyl acetate, ethyl formate, formic acid, heptane, isobutyl acetate, isopropyl acetate, methyl acetate, methyl-1-butanol, methylethyl ketone, methylisobutyl ketone, 2-methyl-1-propanol, pentane, 1-pentanol, 1-propanol, 2-propanol, or propyl acetate.

Other materials that can be used as water immiscible solvents in the invention include: Captex 100: Propylene Glycol Dicaprate; Captex 200: Propylene Glycol Dicaprylate/Dicaprate; Captex 200 P: Propylene Glycol Dicaprylate/Dicaprate; Propylene Glycol Dicaprylocaprate; Captex 300: Glyceryl Tricaprylate/Caprate; Captex 300 EP/NF: Glyceryl Tricaprylate/Caprate Medium Chain Triglycerides; Captex 350: Glyceryl Tricaprylate/Caprate/Laurate; Captex 355: Glyceryl Tricaprylate/Caprate; Captex 355 EP/NF: Glyceryl Tricaprylate/Caprate Medium Chain Triglycerides; Captex 500: Triacetin; Captex 500 P: Triacetin (Pharmaceutical Grade); Captex 800: Propylene Glycol Di (2-Ethylhexanoate); Captex 810 D: Glyceryl Tricaprylate/Caprate/Linoleate; Captex 1000: Glyceryl Tricaprate; Captex CA: Medium Chain Triglycerides; Captex MCT-170: Medium Chain Triglycerides; Capmul GMO: Glyceryl Monooleate; Capmul GMO-50 EP/NF: Glyceryl Monooleate; Capmul MCM: Medium Chain Mono- & Diglycerides; Capmul MCM C8: Glyceryl Monocaprylate; Capmul MCM C10: Glyceryl Monocaprate; Capmul PG-8: Propylene Glycol Monocaprylate; Capmul PG-12: Propylene Glycol Monolaurate; Caprol 10G100: Decaglycerol Decaoleate; Caprol 3G0: Triglycerol Monooleate; Caprol ET: Polyglycerol Ester of Mixed Fatty Acids; Caprol MPGO: Hexaglycerol Dioleate; Caprol PGE 860: Decaglycerol Mono-, Dioleate.

As used herein, a "surfactant" refers to a compound that comprises polar or charged hydrophilic moieties as well as non-polar hydrophobic (lipophilic) moieties; i.e., a surfactant is amphiphilic. The term surfactant may refer to one or a mixture of compounds. A surfactant can be a solubilizing agent, an emulsifying agent or a dispersing agent. A surfactant can be hydrophilic or hydrophobic.

The hydrophilic surfactant can be any hydrophilic surfactant suitable for use in pharmaceutical compositions. Such surfactants can be anionic, cationic, zwitterionic or non-ionic, although non-ionic hydrophilic surfactants are presently preferred. As discussed above, these non-ionic hydrophilic surfactants will generally have HLB values greater than about 10. Mixtures of hydrophilic surfactants are also within the scope of the invention.

Similarly, the hydrophobic surfactant can be any hydrophobic surfactant suitable for use in pharmaceutical compositions. In general, suitable hydrophobic surfactants will have an HLB value less than about 10. Mixtures of hydrophobic surfactants are also within the scope of the invention.

Examples of additional suitable solubilizer include: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide); amides, such as 2-pyrrolidone, 2-piperidone, caprolactam, N-alkylpyrrolidone, N-hydroxyalkylpyrrolidone, N-alkylpiperidone, N-alkylcaprolactam, dimethylacetamide, and polyvinypyrrolidone; esters, such as ethyl propionate, tributylcitrate,acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, valerolactone and isomers thereof, butyrolactone and isomers thereof; and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol nonoethyl ether (available from Gattefosse under the trade name Transcutol), and water. Mixtures of solubilizers are also within the scope of the invention.

Except as indicated, compounds mentioned herein are readily available from standard commercial sources.

The clear liquid composition is visually clear to the unaided eye, as it will contain less than 5%, less than 3% or less than 1% by wt. of suspended solids based upon the total weight of the composition.

Although not necessary, a composition or kit of the present invention may include a chelating agent, preservative, antioxidant, adsorbents, acidifying agent, alkalizing agent, antifoaming agent, buffering agent, colorant, electrolyte, salt, stabilizer, tonicity modifier, diluent, other pharmaceutical excipient, or a combination thereof.

As used herein, the term "antioxidant" is intended to mean an agent that inhibits oxidation and is thus used to prevent the deterioration of preparations by the oxidative process. Such compounds include, by way of example and without limitation, ascorbic acid, ascorbic palmitate, Vitamin E, Vitamin E derivative, butylated hydroxyanisole, butylated hydroxytoluene, hypophosphorous acid, monothioglycerol, propyl gallate, sodium ascorbate, sodium bisulfite, sodium formaldehyde sulfoxylate, sodium metalbisulfite and other such materials known to those of ordinary skill in the art.

As used herein, the term chelating agent is intended to mean a compound that chelates metal ions in solution. Exemplary chelating agents include EDTA (tetrasodium ethylenediaminetetraacetate), DTPA (pentasodium diethylenetriaminepentaacetate), HEDTA (trisodium salt of N-(hydroxyethyl)-ethylene-diaminetriacetic acid), NTA (trisodium nitrilotriacetate), disodium ethanoldiglycine ($Na_2EDG$), sodium diethanolglycine (DEGNa), citric acid, and other compounds known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide an alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium. Such compounds include, by way of example and without limitation, acetic acid, amino acid, citric acid, fumaric acid and other alpha-hydroxy acids, hydrochloric acid, ascorbic acid, and nitric acid and others known to those of ordinary skill in the art.

As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

As used herein, the term "buffering agent" is intended to mean a compound used to resist a change in pH upon dilution or addition of acid or alkali. Such compounds include, by way of example and without limitation, potassium metaphosphate, potassium phosphate, monobasic sodium acetate and sodium citrate anhydrous and dehydrate and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl, or butyl parabens and others known to those of ordinary skill in the art.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, FD&C Green No. 5, FD&C Orange No. 5, FD&C Red No. 8, caramel, and iron oxide (black, red, yellow), other FD&C dyes and natural coloring agents such as grape skin extract, beet red powder, beta-carotene, annato, carmine, turmeric, paprika, combinations thereof and other such materials known to those of ordinary skill in the art.

As used herein, the term "stabilizer" is intended to mean a compound used to stabilize an active agent against physical, chemical, or biochemical processes that would otherwise reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those or ordinary skill in the art.

The composition of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The composition can also include alcohol such as ethanol, isopropanol, hexadecyl alcohol, glycerol and propylene glycol; glycerol ketals such as 2,2-dimethyl-1,3-dioxolane-4-methanol; ethers such as poly(ethylene glycol) 450; petroleum hydrocarbons such as mineral oil and petrolatum; water; a pharmaceutically suitable surfactant, suspending agent or emulsifying agent; or mixtures thereof.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

One or more of the components of the formulation can be present in its free base or pharmaceutically or analytically acceptable salt form. As used herein, "pharmaceutically or analytically acceptable salt" refers to a compound that has been modified by reacting it with an acid as needed to form an ionically bound pair. Examples of acceptable salts include conventional non-toxic salts formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Lists of other suitable salts are found in *Remington's Pharmaceutical Sciences,* $17^{th}$. ed., Mack Publishing Company, Easton, Pa., 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

A dosage form can be made by any conventional means known in the pharmaceutical industry. A liquid dosage form can be prepared by providing at least one liquid carrier and oleandrin or oleandrin-containing extract in a container. One or more other excipients can be included in the liquid dosage form. A solid dosage form can be prepared by providing at least one solid carrier and oleandrin or oleandrin-containing extract. One or more other excipients can be included in the solid dosage form.

A dosage form can be packaged using conventional packaging equipment and materials. It can be included in a pack, bottle, via, bag, syringe, envelope, packet, blister pack, box, ampoule, or other such container.

The invention includes a method for improving the clinical status of a statistically significant number of subjects of in a population of subjects having a neurological condition, the method comprising: administering to the population of subjects an extract of *Nerium* species or *Thevetia* species, or a composition thereof; and determining the clinical status of the subjects to establish the improved clinical status. In some embodiments, the statistically significant number is at least 5%, at least 10%, at least 20%, at least 30%, at least 40%, at least 50%, at least 60%, at least 70%, at least 80% or at least 90% of the population. In some embodiments, the extract comprises one or more other pharmacologically active compounds. In other embodiments, the extract comprises one or more other pharmacologically active compounds comprises that cooperate with oleandrin or another cardiac glycoside to improve the clinical status of the subjects.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

Oleandrin can be purchased from Sigma Chemical Co. (St. Louis, Mo.).

Example 1

Supercritical Fluid Extraction of Powdered Oleander Leaves

Method A. with Carbon Dioxide.

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.94 kg.

The starting material was combined with pure $CO_2$ at a pressure of 300 bar (30 MPa, 4351 psi) and a temperature of 50° C. (122° F.) in an extractor device. A total of 197 kg of $CO_2$ was used, to give a solvent to raw material ratio of 50:1. The mixture of $CO_2$ and raw material was then passed through a separator device, which changed the pressure and temperature of the mixture and separated the extract from the carbon dioxide.

The extract (65 g) was obtained as a brownish, sticky, viscous material having a nice fragrance. The color was likely caused by chlorophyll. For an exact yield determination, the tubes and separator were rinsed out with acetone and the acetone was evaporated to give an addition 9 g of extract. The total extract amount was 74 g. Based on the weight of the starting material, the yield of the extract was 1.88%. The content of oleandrin in the extract was calculated using high pressure liquid chromatography and mass spectrometry to be 560.1 mg, or a yield of 0.76%.

Method B. with Mixture of Carbon Dioxide and Ethanol

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.85 kg.

The starting material was combined with pure $CO_2$ and 5% ethanol as a modifier at a pressure of 280 bar (28 MPa, 4061 psi) and a temperature of 50° C. (122° F.) in an extractor device. A total of 160 kg of $CO_2$ and 8 kg ethanol was used, to give a solvent to raw material ratio of 43.6 to 1. The mixture of $CO_2$, ethanol, and raw material was then passed through a separator device, which changed the pressure and temperature of the mixture and separated the extract from the carbon dioxide.

The extract (207 g) was obtained after the removal of ethanol as a dark green, sticky, viscous mass obviously containing some chlorophyll. Based on the weight of the starting material, the yield of the extract was 5.38%. The content of oleandrin in the extract was calculated using high pressure liquid chromatography and mass spectrometry to be 1.89 g, or a yield of 2.1%.

Example 2

Hot-Water Extraction of Powdered Oleander Leaves

Hot water extraction is typically used to extract oleandrin and other active components from oleander leaves. Examples of hot water extraction processes can be found in U.S. Pat. Nos. 5,135,745 and 5,869,060.

A hot water extraction was carried out using 5 g of powdered oleander leaves. Ten volumes of boiling water (by weight of the oleander starting material) were added to the powdered oleander leaves and the mixture was stirred constantly for 6 hours. The mixture was then filtered and the leaf residue was collected and extracted again under the same conditions. The filtrates were combined and lyophilized. The appearance of the extract was brown. The dried extract material weighed about 1.44 g. 34.21 mg of the extract material was dissolved in water and subjected to oleandrin content analysis using high pressure liquid chromatography and mass spectrometry. The amount of oleandrin was determined to be 3.68 mg. The oleandrin yield, based on the amount of extract, was calculated to be 0.26%. The table below shows a comparison between the oleandrin yields for the two supercritical carbon dioxide extractions of Example 1 and the hot water extraction.

Comparison of Yields

| Extraction Medium | Oleandrin yield based on total extract weight |
|---|---|
| Supercritical Carbon Dioxide: Example 1, Method A | 0.76% |
| Supercritical Carbon Dioxide: Example 1, Method B | 2.1% |
| Hot Water Extraction: Example 2 | 0.26% |

Example 3

Treatment of Neurological Condition Including but not Limited to Alzheimer's Disease Method A. Extract Therapy A subject presenting with Alzheimer's disease is prescribed cardiac glycoside, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with the extract, or fraction or sub-fraction thereof, is continued as needed and the dose or dosing regimen can be adjusted as needed until the patient reaches the desired clinical endpoint.

Method B. Combination Therapy: Extract and Another Therapeutic Agent

Method A, above, is followed except that the subject is prescribed and administered one or more other therapeutic agents for the treatment of Alzheimer's disease, or symptoms thereof. Then one or more other therapeutic agents can be administered before, after or with the extract. Dose escalation (or de-escalation) of the one or more other therapeutic agents can also be done. Suitable one or more other therapeutic agents include Namenda™ (memantine HCl), Aricept™ (donepezil), Razadyne™ (galantamine), Exelon™ (rivastigmine), Cognex™ (tacrine), and amantadine.

Example 4

Treatment of Neurological Condition Including but not Limited to Huntington's Disease Method A. Extract Therapy A subject presenting with Huntington's disease is prescribed the extract, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with extract is continued as needed and the dose or dosing regimen can be adjusted as needed until the patient reaches the desired clinical endpoint. The doses administered can be similar to those of Example 3 or as otherwise described herein.

Method B. Combination Therapy: Extract and Another Therapeutic Agent

Method A, above, is followed except that the subject is prescribed and administered one or more other therapeutic agents for the treatment of Huntington's disease, or symptoms thereof. The one or more other therapeutic agents can be administered before, after or with the cardiac glycoside. Dose escalation (or de-escalation) of the one or more other therapeutic agents can also be done. Suitable one or more other therapeutic agents include Vitamin E, Baclofen (a derivative of CoQ10), Lamotrigine (an anticonvulsant), remacemide (an anesthetic which is a low affinity NMDA antagonist), and riluzole (Na channel blocker).

Example 5

Treatment of Neurological Condition Including but not Limited to Ischemic Stroke Method A. Extract Therapy A subject presenting with ischemic stroke is prescribed the extract, and therapeutically relevant doses are administered to the subject according to a prescribed dosing regimen for a period of time. The subject's level of therapeutic response is determined periodically. If the level of therapeutic response is too low at one dose, then the dose is escalated according to a predetermined dose escalation schedule until the desired level of therapeutic response in the subject is achieved. Treatment of the subject with the extract is continued as needed and the dose or dosing regimen can be adjusted as needed until the patient reaches the desired clinical endpoint. The doses administered can be similar to those in Example 3 or as otherwise described herein.

Method B. Combination Therapy: Extract and Another Therapeutic Agent

Method A, above, is followed except that the subject is prescribed and administered one or more other therapeutic agents for the treatment of ischemic stroke, or symptoms thereof. The one or more other therapeutic agents can be administered before, after or with the extract. Dose escalation (or de-escalation) of the one or more other therapeutic agents can also be done.

Example 6

HPLC Analysis of Solutions Containing Oleandrin

Samples (oleandrin standard, SCF extract and hot-water extract) were analyzed on HPLC (Waters) using the following conditions: Symmetry C18 column (5.0 μm, 150×4.6 mm I.D.; Waters); Mobile phase of MeOH:water=54:46 (v/v) and flow rate at 1.0 ml/min. Detection wavelength was set at 217 nm. The samples were prepared by dissolving the compound or extract in a fixed amount of HPLC solvent to achieve an approximate target concentration of oleandrin.

Example 7

Determination of α3 and α1 Expression in Normal Neuronal Tissue

The procedures set forth in PCT International Application No. PCT/US08/82641, filed Nov. 6, 2008 in the name of Phoenix Biotechnology, Inc., the entire disclosure of which is hereby incorporated by reference, can be followed.

Example 8

Evaluation of a Cardiac Glycoside and an Extract of the Invention in an In Vitro Assay for Stroke and Non-Stroke Method A. Stroke: Preparation of Cortical Brain Slices and OGD.

Neocortical brain slices were prepared from PND 7 Sprague-Dawley rat pups. The cerebral cortex was dissected, cut into 400-μ-thick slices and transferred into a container containing cold artificial cerebrospinal fluid with 1 μM MK-801 before plating; MK-801 was not included in any subsequent procedures. To mimic ischemic injury using transient oxygen-glucose deprivation (OGD), slices from one hemisphere of each brain were exposed to glucose-free, $N_2$-bubbled artificial cerebrospinal fluid for 7.5 min in a low $O_2$ (0.5%) environment. The OGD slices were then plated side-by-side with control slices from the contralateral hemisphere on nitrocellulose or Millicell (Millipore) permeable membranes, which were prepared identically except for no OGD. Thirty minutes after plating, the brain slice pairs were transfected, transferred to 24-well plates, and incubated at 37° C. under 5% $CO_2$ in humidified chambers. In each experiment, 5-6 minutes of oxygen-glucose deprivation (OGD) was used to induce >50% loss of healthy cortical neurons by 24 hrs. A set concentration (3 μM) of neriifolin (a cardiac glycoside) was used as the internal positive control. For oleandrin (a cardiac glycoside), all three concentrations from 0.3 to 3 μM appeared to provide neuroprotection in the first two experiments, so the oleandrin concentrations tested were lowered in the third run and suggested that the threshold concentration for neuroprotection lies between 0.1 and 0.3 μM. The unfractionated extract, e.g. of *Nerium* species, or a fraction thereof can also be used as described for the oleandrin.

Method B. Non-Stroke: Brain Slice Assay.

Oleandrin and PBI-05204, an unfractionated SCF extract of *Nerium oleander*, were tested on "nonstroked" brain slices; that is, ones that were sliced and transfected with YFP but not subjected to additional trauma via OGD. See experimental procedure outlined above. We have observed that a number of neuroprotective compounds, including neriifolin, can provide modest levels of neuroprotection to such brain slices, presumably by protecting against the trauma caused by the process of slicing and culturing itself. The data demonstrate that oleandrin and the extract appeared to be able to provide neuroprotection to such "non-OGD" brain slices to similar levels as neriifolin signifying that cardiac glycosides mediate neuroprotection even in the absence of oxygen or glucose deprivation.

Example 9

Evaluation of a Cardiac Glycoside and an Extract in an In Vitro Assay for Alzheimer's Disease In the rat brain slice model for APP/Abeta-induced degeneration of cortical pyramidal neurons biolistic transfection is used not only to introduce vital markers such as YFP, but also to introduce disease gene constructs into the same neuronal populations in the brain slices. Thus, the APP/Aβ brain slice model co-transfects YFP with APP isoforms, leading to the progressive degeneration of cortical pyramidal neurons over the course of 3-4 days after brain slice preparation and transfection. The data demonstrate that both oleandrin and PBI-05204, an unfractionated SCF extract of *Nerium oleander*, appeared able to provide concentration-dependent neuroprotection to APP-transfected brain slices, rescuing to levels nearly to those that can be provided by BACE inhibitor drugs.

Example 10

Evaluation of a Cardiac Glycoside and an Extract in an In Vitro Corticostriatal Co-Culture Assay for Huntington's Disease In this assay, instead of using intact brain slices, mutant htt is introduced via electroporation into high-density, mixed co-cultures of cortical neurons, striatal neurons, and glia arrayed in 96-well plates. The goal of this assay platform is to combine the biological/clinical relevance of a complex primary culture system that recapitulates key aspects of the interconnectivity of disease-relevant neuronal populations in vivo, with the ability to conduct large-scale fully automated screening campaigns. In this assay, over the course of 1-2 weeks in vitro, transfected mutant htt constructs induce the progressive degeneration of both striatal and cortical neurons that are subsequently quantified using automated image acquisition and object detection algorithms on the Cellomics Arrayscan VTI platform. Each data point was drawn from 6 wells with 16 images in each well automatically captured, processed, and analyzed on the Cellomics Arrayscan using protocols developed during a large-scale screening campaign being conducted in association with the Cure Huntington's Disease Initiative. In a full run, some 25,000 images are collected and analyzed in each cycle, 4 cycles per week.

Cortico-Striatal Co-Culture Assay Platform.

Pure glial cultures are prepared in advance of neuronal plating to establish 96-well plates with confluent glial beds. Cortical and striatal tissue are then dissociated separately and "nucleofected" with appropriate DNA constructs and are distinguishable later by the expression of different fluorescent proteins such as YFP, CFP, and mCherry. These separately transfected cortical and striatal neurons are then mixed thoroughly and plated into the 96-well plates containing the previously plated glial monolayers.

Both oleandrin and PBI-05204 (the supercritical $CO_2$ extract of *Nerium oleander*) were tested in this cortico-striatal co-culture platform and preliminarily these compounds appear to be the strongest hits we have observed to date out of >400 late-stage drug molecules that have been evaluated in this assay system. For comparison, a dose-response graph for KW6002 (an adenosine 2a receptor antagonist), the compound that we routinely include as the positive control for this co-culture assay is included. Efficacy of oleandrin is on par with KW6002, while its potency appears to be some 100-fold greater (FIGS. 3A-3D).

Example 11

Evaluation of a Fraction of an SCF Extract of *Nerium oleander* in an In Vitro APP Assay for Alzheimer's Disease The fraction was prepared according to Example 13. This assay was conducted similar to that of Example 9. The data in FIG. 6 demonstrate that there is a concentration dependent effect of Fraction O-4A in preventing the neurodegeneration associated with introduction of the APP construct. In particular, the data demonstrate neuroprotection between the concentration range of 3 to 30 ug/ml.

Example 12

Evaluation of a Fraction of an SCF Extract of *Nerium oleander* in an In Vitro Tau4R Assay for Alzheimer's Disease The fraction was prepared according to Example 13. The data in FIG. 7 demonstrate that there is a concentration dependent effect of Fraction O-4A in preventing the neurodegeneration associated with introduction of the Tau construct. In particular, the data demonstrate a neuroprotection between the concentration range of 3 to 30 ug/ml. There is a significant difference between Tau construct treated cells and those exposed to solutions of Fraction 0-4A.

Example 13

Chromatographic Fractionation of SCF Extract

A supercritical extract (5 g) of oleander leaves (obtained as described herein by extracting a plant mass with a mixture of supercritical $CO_2$ with EtOH added as a cosolvent/modifier, Batch #270111) was suspended in water (150 mL) and partitioned three times with hexane (150 ml each time). The water layer was subjected to ODS C-18 (octadecyl-functionalized silica gel, 20-22% labeled, 200-400 mesh) open column (400 mm (L)×38 mm (ID)) fractionation by charging the water layer directly to a bed of the ODS resin equilibrated with water. The column was treated successively with mixtures of water and methanol (1000 ml of 30% methanol in water, 1000 ml of 55% methanol in water, 1000 ml of 80% methanol in water, 1000 ml of 100% methanol) and with a mixture of acetone:methanol (2 volumes: 1 volume; 1000 ml). The effluent (1000 mL) from each mixture was collected. The solvent was removed from each fraction by evaporation to yield five fractions, namely Fr-O-1, Fr-O-2, Fr-O-3, Fr-O-4, and Fr-O-5. The fractions were then analyzed by HPLC chromatography as per Example 14.

Example 14

HPLC Analysis of Fractions of SCF Extract

The purpose of this assay was to identify extract fractions (from above) containing cardiac glycoside. A sample from each fraction obtained according to Example 13 was analyzed as follows. The fraction 1-3 mg) was dissolved in 1-5 ml of aqueous methanol (80% methanol in water). The diluted sample (10-25 μl) was analyzed with an Agilent Zorbax SB-C18 column using 80% methanol in water as the mobile phase, a flow rate of 0.7 mL/min and DAD-UV effluent monitoring at the following wavelengths: 203, 210, 217, 230, 254, 280, 310 and 300 nm.

Example 15

Figure 4A:
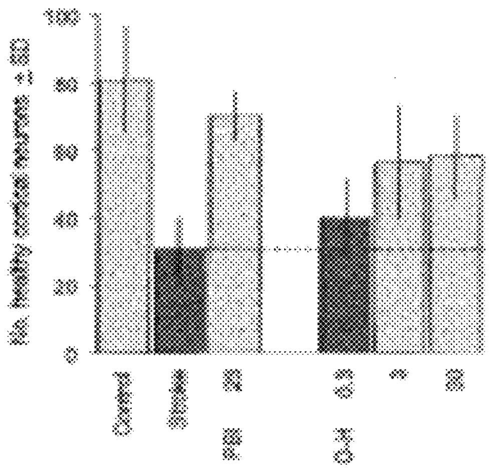
FIGS. 4A-4E depict the results of a neuroprotection brain-slice-based "stroke" assay as described herein, wherein the oleandrin-containing SCF extract has been fractionated via liquid chromatography (Example 13) and the five different fractions (described below) subjected to this assay (Example 15): Fraction O—H (FIG. 4A), Fraction O-2 (FIG. 4B), Fraction O-3 (FIG. 4C), Fraction O-4 (FIG. 4D), Fraction O-5 (FIG. 4E).
Figure 4B:
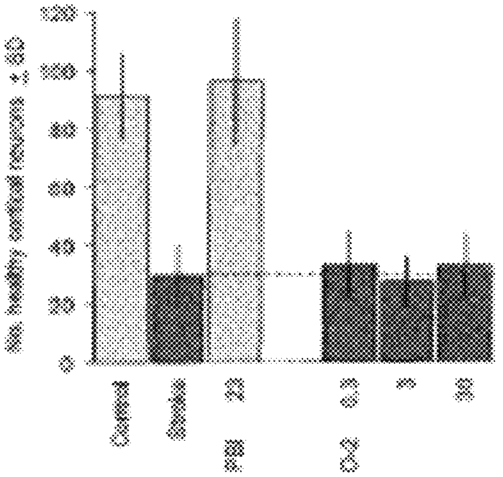
Figure 4C:
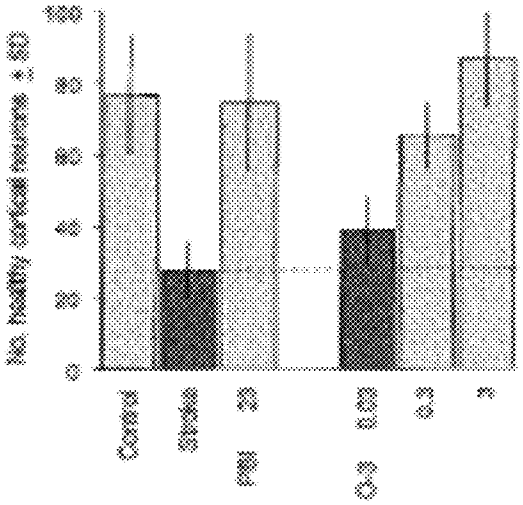
Figure 4D:
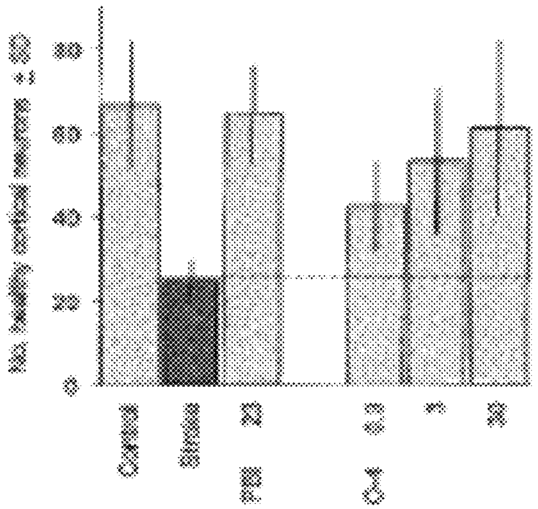
Figure 4E:
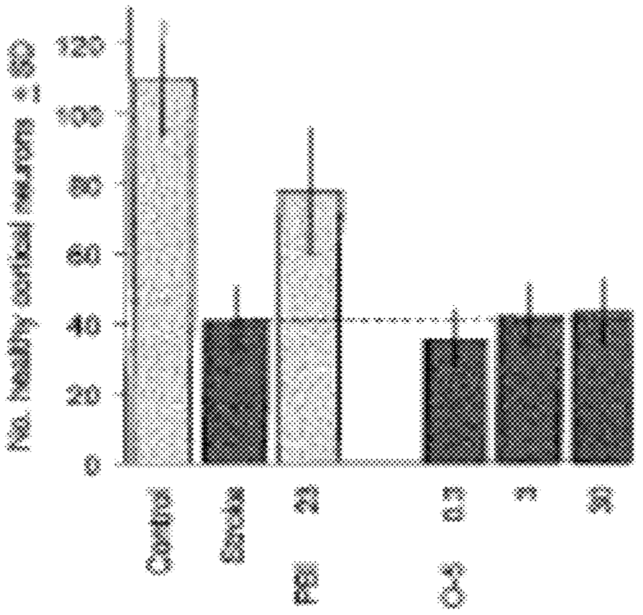

Brain-Slice Assay for Determination of Neuroprotection Provided by Fractions of Extract This assay was conducted according to Example 8. The data demonstrate that compared to untreated stroke (OGD) mediated damage to brain slice neurons PBI-05204 provides a significant level of protection. A similar level of neuroprotection was provided by Fraction 0-4A (FIGS. 4A and 5) as well as Fraction 0-3 (FIG. 4C) and Fraction 0-1 (FIG. 4D). In contrast, Fractions 0-2 (FIG. 4B) and 0-5 (FIG. 4E) demonstrated no neuroprotective effects in this OGD model of stroke mediated ischemic brain injury.

Example 16

Time-Delay Brain-Slice Assay for Determination of Neuroprotection

This assay was conducted according to Example 8 except that the following changes were made. A specified length of time was allowed between OGD and introduction of a proposed neuroprotective agent. The ability of PBI-05204 to provide neuroprotection to brain slices if treatment was delayed relative to the timing of the OGD treatment was determined. Data showed that a 2 hr delay of *Nerium oleander* extracts was well tolerated, showing similar levels of neuroprotection to those attained with application of PBI-05204 immediately following OGD treatment. Neuroprotective benefit was reduced with 4 to 6 hr of delay of administration of PBI-05204, but at levels of neuroprotection that were still significantly and physiologically relevant.

Example 17

Identification of Compounds in a Fraction of *Nerium oleander* SCF Extract Obtained According to Example 13

The water and methanol present in the Fr-O-4 fraction were removed by evaporation under reduced pressure. The residue from the Fr-O-4 fraction of Example 13 was subjected to silica gel chromatography (below) to provide sub-fractions that were then analyzed by thin layer chromatography (TLC). Fractions having similar TLC profiles were combined and the solvents thereof removed by evaporation under reduced pressure. The remaining residues were analyzed by HNMR.

Thin Layer Chromatography

TLC was performed on conventional analytical grade TLC plates using a mixture of hexane:ethyl acetate (7:3 v:v). The compounds were visualized with $H_2SO_4$, whereby steroids exhibit a blue color and triterpenes exhibit a purple color.

Prior to further fractionation by flash chromatography, TLC analysis of the Fr-O-4 fraction indicated the presence of one major spot and more than five small spots. The color reaction indicated that the major spot contained a mixture of steroid and triterpene and most of the small spots contained steroids.

Silica Gel Flash Chromatography

Silica gel (Biotage; (10-15 g) was loaded into a column and equilibrated with a mixture of ethyl acetate (3%) and hexane (97%). The residue from the Fr-O-4 fraction was taken up in mixture 0.2-0.5 ml] of ethyl acetate (3%) and hexane (97%) and charged onto the column. Flash chromatography was conducted using a solvent gradient of ethyl acetate (3%-30%) in hexane (97%-70%, respectively) followed by 100% methanol. Sub-fractions collected from the column were analyzed by TLC (above) and those fractions having similar TLC visualization profiles were combined and concentrated to remove solvent.

HNMR Spectroscopy

A sample of each of the concentrated sub-fractions obtained from flash chromatography was analyzed by HNMR using conventional methods so as to determine the structural class for the major components.

Example 18

Identification of Compounds in *Nerium oleander* SCF Extract Obtained According to Example 1 (Method B) in Unfractionated Form The SCF extract was analyzed by MS-DART TOF analysis as follows. A JEOL AccuTOF-DART mass spectrometer (Jeol U.S.A., Peobody, Mass., U.S.A.) was used.

A JEOL AccuTOF-DART mass spectrometer (Jeol USA, Peabody, Mass., USA) was used. Analyses were conducted in a positive ion mode (DART+) giving masses corresponding to the M+H+ ions generated by the DART-MS. A range of settings on the instrument was used to determine optimal conditions for *N. oleander* analyses. The general settings for DART+ included: needle voltage 3500 V; orifice 1-2-20 V; ring lens 2-5 V; orifice 2-2-5 V; and peaks voltage 1000 V. Calibrations were performed internally with each sample using a 10% solution of PEG 600 which provides mass markers throughout the required mass range of 100-1000 mass units. Other analyses were undertaken in the DART-mode and these consisted of: needle voltage 3500 V; heating element 250° C.; electrode 1-150 V; electrode 2-250 V; He gas flow rate 3.79LPM. Mass spectrometer settings: MCP 2600 V; orifice 1-15 V; ring lens-5 V, orifice 2-5 V; and peaks voltage 1000 V. Calibrations were performed internally with each sample using a perfluorinated carboxylic acid solution that provides markers throughout the required mass range of 100-1000 mass units. The *N. oleander* samples were introduced neat into the DART helium plasma using the closed end of a borosilicate glass melting point tube. The capillary tube was held in the He plasma for approximately 3-5 s per analysis. Molecular formulas were confirmed by elemental composition and isotope matching programs provided with the JEOL AccuTOF DART-MS instrument. A searchable database of *N. oleander* constituents, developed by HerbalScience (Naples, Fla., USA) was used.

The SCF extract was found to contain at least the following components present in the indicated relative abundances (%).

| Component | Relative Abundance (%) |
|---|---|
| Oleandrin | 2.99 |
| Oleandrigenin | 3.31 |
| Ursolic acid/betulinic acid | 15.29 |
| Odoroside | 0.80 |
| Oleanolic acid | 0.60 |
| Urs-12-ene-3β,28-diol/betulin | 5.44 |
| 3β,3β-hydroxy-12-olean-en-28-oic acid | 14.26 |
| 28-norurs-12-en-3β-ol | 4.94 |
| Urs-12-en-3β-ol | 4.76 |

As used herein and unless otherwise specified, the term "about" or "approximately" are taken to mean±10%, ±5%, ±2.5% or ±1% of a specified valued. As used herein and unless otherwise specified, the term "substantially" is taken to mean "to a large degree", "at least a majority of", greater than 70%, greater than 85%, greater than 90%, greater than 95%, greater than 98% or greater than 99%.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What is claimed is:

1. A method of treating a neurological condition in a subject comprising: administering to a subject in need thereof a composition comprising an extract of *Nerium* species or of *Thevetia* species in an effective amount to treat said neurological condition, wherein the extract comprises as major components at least one steroid and at least one triterpene extracted from the *Nerium* species or *Thevetia* species, comprises less than 1% wt. of polysaccharide extracted from the *Nerium* species or *Thevetia* species, and the extract excludes oleandrin and neriifolin, wherein the neurological condition is selected from the group consisting of Huntington's disease, stroke, a taupathy or a condition having an etiology associated with excessive proteolysis of amyloid beta precursor protein, with accumulation of amyloid beta protein in the synapses of the neurons of a subject, with formation of amyloid fibrils in the synapses of the neurons of a subject, or with formation of amyloid plaques in the synapses of the neurons of a subject, wherein the neurological condition excludes Alzheimer's disease and multiple sclerosis.

2. The method of claim 1 comprising:

determining whether or not the neurological condition in the subject is Huntington's disease, stroke, a taupathy or a condition having an etiology associated with excessive proteolysis of amyloid beta precursor protein, with accumulation of amyloid beta protein in the synapses of the neurons of a subject, with formation of amyloid fibrils in the synapses of the neurons of a subject, or with formation of amyloid plaques in the synapses of the neurons of a subject, wherein the neurological condition excludes Alzheimer's disease and multiple sclerosis;

indicating administration of an unfractionated extract or a fraction of extract or sub-fraction of extract of *Nerium* species or of *Thevetia* species, wherein the extract, fraction thereof or sub-fraction thereof comprises as major components at least one steroid and at least one triterpene extracted from the *Nerium* species or *Thevetia* species, comprises less than 1% wt. of polysaccharide extracted from the *Nerium* species or *Thevetia* species, and excludes oleandrin and neriifolin;

administering an initial dose of the extract, to the subject according to a prescribed initial dosing regimen for a period of time;

periodically determining the adequacy of subject's clinical response and/or therapeutic response to treatment with the extract; and if the subject's clinical response and/or therapeutic response is adequate, then continuing treatment with the extract, as needed until the desired clinical endpoint is achieved; or if the subject's clinical response and/or therapeutic response are inadequate at the initial dose and initial dosing regimen, then escalating or deescalating the dose until the desired clinical response and/or therapeutic response in the subject is achieved.

3. The invention according to claim 1, wherein the composition further comprises one or more other therapeutically effective agents.

4. The invention according to claim 1, wherein the extract is obtained by extraction of *Nerium* species or *Thevetia* species by hot water extraction, cold water extraction, supercritical fluid extraction, organic solvent extraction or a combination thereof.

5. The invention according to claim 1, wherein the composition comprises a fraction of an extract of *Nerium* species or *Thevetia* species.

6. The invention according to claim 5, wherein the fraction has been prepared by liquid chromatographic fractionation of the extract.

7. The invention according to claim 1, wherein the *Nerium* species is *Nerium oleander* and the *Thevetia* species is *Thevetia neriifolia*.

8. The invention according to claim 1, wherein the composition comprises a sub-fraction of a fraction of an extract of *Nerium* species or *Thevetia* species, wherein the sub-fraction has been prepared by liquid chromatographic fractionation of a fraction of the extract, and the sub-fraction excludes oleandrin and neriifolin.

9. The invention according to claim 1, wherein: 1) the subject is prescribed and administered a therapeutically relevant dose of the composition; and/or 2) the subject is administered the composition according to a prescribed dosing regimen.

10. The invention according to claim 1, wherein: a) the at least one steroid and at least one triterpene function additively or synergistically to contribute to the therapeutic efficacy of the extract when the extract is administered to a subject.

11. The invention according to claim 1, wherein the extract further excludes cardiac glycoside selected from the group consisting of odoroside, neritaloside, ouabain, bufalin, digitoxin, cinobufatalin, cinobufagin, and resibufogenin.

12. The invention according to claim 1, wherein the extract is present in a pharmaceutical formulation or composition.

13. The invention according to claim 1, wherein: a) the extract has been obtained from an oleander plant mass or neriifolia plant mass; b) the plant mass comprises *Nerium* species or *Thevetia* species.

14. The invention according to claim 1, wherein the extract, or fraction thereof or sub-fraction thereof, of *Nerium* species or *Neriifolia* species, exhibits therapeutic activity as described herein when administered to a subject.

15. The method of claim 1, wherein the extract, fraction thereof or sub-fraction thereof comprises betulin (urs-12-ene-3β,28-diol); 28-norurs-12-en-3β-ol; urs-12-en-3β-ol; 3β,3β-hydroxy-12-oleanen-28-oic acid; 3β,20α-dihydroxyurs-21- en-38-oic acid; 3β,27-dihydroxy-12-ursen-38-oic acid; 3β,13β-dihydroxyurs-11-en-28-oic acid; 3β,12α-dihydroxy-oleanan-28,13β-olide; 3β,27-dihydroxy-12-oleanan-28-oic acid; less than 1% wt. of polysaccharide extracted from the *Nerium* species or *Thevetia* species, and excludes oleandrin and neriifolin.

16. A method for improving the clinical status of a statistically significant number of subjects of in a population of subjects having a neurological condition, the method comprising: administering to the population of subjects an extract of *Nerium* species or of *Thevetia* species, wherein the extract is unfractionated, a fraction thereof or a sub-fraction or a fraction thereof; and determining the clinical status of the subjects, wherein the extract, fraction thereof or sub-fraction thereof comprises as major components at least one steroid and at least one triterpene extracted from the *Nerium* species or *Thevetia* species, comprises less than 1% wt. of polysaccharide extracted from the *Nerium* species or *Thevetia* species, and excludes oleandrin and neriifolin, and wherein the neurological condition excludes Alzheimer's disease and multiple sclerosis.

17. A method of reducing the incidence of occurrence of a neurological condition in a population of subjects at risk thereof, the method comprising administering an effective dose of extract, fraction thereof or sub-fraction thereof of *Nerium* species or *Thevetia* species on a recurring basis for an extended period of time to one or more subjects in a population of subjects at risk of suffering from a neurological condition selected from the group consisting of Huntington's disease and stroke, thereby reducing the incidence of the neurological condition in the population, wherein the extract, fraction thereof or sub-fraction thereof comprises as major components at least one steroid and at least one triterpene extracted from the *Nerium* species or *Thevetia* species, comprises less than 1% wt. of polysaccharide extracted from the *Nerium* species or *Thevetia* species, and excludes oleandrin and neriifolin, and wherein the neurological condition excludes Alzheimer's disease and multiple sclerosis.

18. The method of claim 17, wherein the method further comprises periodically determining the adequacy of one or more subject's clinical response and/or therapeutic response to treatment with the extract; and if the subject's clinical response and/or therapeutic response is adequate, then the method further comprises continuing treatment with the extract as needed until the desired clinical endpoint is achieved; or if the subject's clinical response and/or therapeutic response are inadequate at the initial dose and initial dosing regimen, then the method further comprises escalating or deescalating the dose until the desired clinical response and/or therapeutic response in the subject is achieved.

19. The method of claim 17, wherein the method further comprises identifying a population of subjects at risk of suffering from the neurological condition.

20. The method of claim 19, wherein the population of subjects at risk is characterized by advancing age of the subject, familial history of the neurological condition, genetic predisposition to occurrence of neurological condition, the presence and expression of ApoE4 gene in the subject, female gender, cardiovascular disease, diabetes, Down's Syndrome, head injury, low levels of formal education, smoking, excessive alcohol consumption and/or drug abuse.

21. The method of claim 17, wherein: a) the method further comprises indicating administration of the extract to the one or more subjects; b) the method further comprises administering an effective dose of the extract to the subject according to a prescribed dosing regimen for a period of time; and/or c) the extract is administered to plural subjects in a population.

22. The method of claim 17, wherein: a) the recurring basis is daily, every other day, every second day, every third day, every fourth day, every fifth day, every sixth day, weekly, every other week, every second week, every third week, monthly, bimonthly, semi-monthly, every other month every second month, quarterly, every other quarter, trimesterly, seasonally, semi-annually and/or annually; b) the extended period is one or more weeks, one or more months, one or more quarters and/or one or more years; and/or c) the effective dose is administered one or more times in a day.

23. A time-delayed method of treating stroke in a subject comprising:

within a delay period after a subject has suffered the stroke, administering an initial dose of extract, or fraction thereof or sub-fraction thereof of *Nerium* species or *Thevetia* species according to an initial dosing regimen, wherein the extract, fraction thereof or sub-fraction thereof comprises as major components at least one steroid and at least one triterpene extracted from the *Nerium* species or *Thevetia* species, comprises less than 1% wt. of polysaccharide extracted from the *Nerium* species or *Thevetia* species, and excludes oleandrin and neriifolin;

determining the adequacy of subject's clinical response and/or therapeutic response to treatment with the extract; and if the subject's clinical response and/or therapeutic response is adequate, then continuing treatment with extract as needed until the desired clinical endpoint is achieved; or if the subject's clinical response and/or therapeutic response are inadequate at the initial dose and initial dosing regimen, then escalating or deescalating the dose until the desired clinical response and/or therapeutic response in the subject is achieved.

24. The method of claim 23, wherein the delay period is 10 hours or less, 8 hours or less, 6 hours or less, 4 hours or less, 3 hours or less, 2 hours or less, 1 hour or less, 45 minutes or less, 30 minutes or less, 20 minutes or less or 10 min or less.

25. The method of claim 23, wherein determining the adequacy of a subject's clinical and/or therapeutic response is done by assessments of any weakness of the face, arm and/or leg on one side of the body, numbness in the face, arm, and/or leg on one side of the body, inability to understand spoken language, inability to speak or speak clearly, inability to write, vertigo and/or gait imbalance, double vision and an unusually severe headache.

26. A method of treating a neurological condition in a subject comprising: administering to a subject in need thereof a composition comprising an extract of *Nerium* species or of *Thevetia* species in an effective amount to treat said neurological condition, wherein the extract comprises one or more therapeutically effective agents extracted from the *Nerium* species or *Thevetia* species, comprises less than 1% wt. of polysaccharide extracted from the *Nerium* species or *Thevetia* species and the extract excludes oleandrin and neriifolin, and wherein the extract, or fraction thereof or sub-fraction thereof, of *Nerium* species or *Neriifolia* species, has a $^{1}$HNMR spectrum as described in FIGS. 9B-9I.

27. A method of treating a neurological condition in a subject comprising: administering to a subject in need thereof a composition comprising an extract of *Nerium* species or of *Thevetia* species in an effective amount to treat said neurological condition, wherein the extract comprises one or more therapeutically effective agents extracted from the *Nerium* species or *Thevetia* species, comprises less than 1% wt. of polysaccharide extracted from the *Nerium* species or *Thevetia* species and the extract excludes oleandrin and neriifolin, and wherein the extract, or fraction thereof or sub-fraction thereof, of *Nerium* species or *Neriifolia* species, has a HPLC chromatogram as described in FIG. 8D.

28. The method of claim 1, 15 or 19, wherein the extract comprises at least one steroid, at least two triterpenes and less than 1% wt. of polysaccharide extracted from the *Nerium* species or *Thevetia* species, and excludes oleandrin and neriifolin.

29. The method of claim 1, 15 or 19, wherein the extract comprises at least two steroids, at least two triterpenes and less than 1% wt. of polysaccharide extracted from the *Nerium* species or *Thevetia* species, and excludes oleandrin and neriifolin.

30. The method of claim 1, 16 or 19, wherein the extract, fraction thereof or sub-fraction thereof comprises oleandrigenin, ursolic acid, betulinic acid, odoroside, neritaloside, oleanolic acid and one or more triterpenes and less than 0.5% by weight polysaccharide extracted from the *Nerium* species or *Thevetia* species, and excludes oleandrin and neriifolin.

* * * * *